United States Patent
Lodge et al.

(10) Patent No.: US 8,235,963 B2
(45) Date of Patent: Aug. 7, 2012

(54) DISPOSABLE WEARABLE ABSORBENT ARTICLES WITH ANCHORING SYSTEMS

(75) Inventors: Richard Worthington Lodge, Colerain Township, OH (US); Fred Naval Desai, Fairfield, OH (US); Donald Carroll Roe, West Chester, OH (US); Bruno Johannes Ehrnsperger, Bad Soden (DE); Anna Macura, Cincinnati, OH (US); Fred Langdon, Blue Ash, OH (US); Luke Magee, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 216 days.

(21) Appl. No.: 11/599,851

(22) Filed: Nov. 15, 2006

(65) Prior Publication Data

US 2007/0287982 A1    Dec. 13, 2007

Related U.S. Application Data

(60) Provisional application No. 60/811,580, filed on Jun. 7, 2006.

(51) Int. Cl.
*A61F 13/64* (2006.01)

(52) U.S. Cl. ............ 604/392; 604/385.27; 604/402

(58) Field of Classification Search .......... 604/389, 604/392, 394, 395, 401, 402, 385.27–385.28
See application file for complete search history.

(56) References Cited

U.S. PATENT DOCUMENTS

| | | | | |
|---|---|---|---|---|
| 84,703 A * | 12/1868 | Moore | ............ | 604/394 |
| 1,155,659 A * | 10/1915 | Johnson | .......... | 604/402 |
| 1,157,774 A * | 10/1915 | Goodnou | ........ | 604/398 |
| 1,485,001 A * | 2/1924 | Wills | ............ | 604/392 |
| 1,487,154 A * | 3/1924 | Filiatrault | ........ | 604/402 |
| 1,609,769 A * | 12/1926 | Perlzweig | ....... | 604/401 |
| 1,661,936 A * | 3/1928 | Ferstl | ............ | 604/401 |
| 1,705,194 A * | 3/1929 | Marinsky | ....... | 604/400 |
| 1,756,508 A * | 4/1930 | Bersin | .......... | 604/392 |
| 1,917,979 A | 7/1933 | Kelly | | |
| 1,919,124 A * | 7/1933 | Panullo | ........ | 604/401 |
| 2,025,843 A * | 12/1935 | Anderson | ...... | 604/392 |
| 2,092,409 A * | 9/1937 | Solar | ............ | 604/402 |
| 2,126,905 A * | 8/1938 | McCracken | ...... | 604/397 |
| 2,493,113 A * | 1/1950 | Dance | .......... | 604/394 |
| 2,572,331 A * | 10/1951 | Gillessen | ........ | 604/397 |
| 2,652,058 A | 9/1953 | Carpenter | | |
| 2,699,171 A | 1/1955 | McWilliams | | |
| 2,863,455 A * | 12/1958 | Holce | .......... | 604/398 |

(Continued)

FOREIGN PATENT DOCUMENTS

EP    0323634 A2    12/1989

(Continued)

OTHER PUBLICATIONS

U.S. Appl. No. 11/810,901, filed Jun. 7, 2007, Lodge, et al.

(Continued)

*Primary Examiner* — Melanie Hand
*Assistant Examiner* — Paula Craig
(74) *Attorney, Agent, or Firm* — Charles R. Ware

(57) ABSTRACT

Embodiments of the present disclosure include disposable wearable absorbent articles with anchoring systems. In an embodiment, a disposable wearable absorbent article includes an absorbent core and an anchoring system configured to anchor the absorbent core to a wearer.

14 Claims, 27 Drawing Sheets

U.S. PATENT DOCUMENTS

| | | | |
|---|---|---|---|
| 2,891,545 A * | 6/1959 | Teague | 604/402 |
| 3,014,482 A * | 12/1961 | Case | 604/402 |
| 3,022,788 A * | 2/1962 | Darcey | 450/105 |
| 3,073,309 A * | 1/1963 | Mosier | 604/402 |
| 3,375,826 A * | 4/1968 | Field | 604/402 |
| 3,441,025 A | 4/1969 | Ralph | |
| 3,635,221 A | 1/1972 | Champaigne | |
| 3,658,064 A | 4/1972 | Pociluyko | |
| 3,825,006 A | 7/1974 | Ralph | |
| 3,848,594 A | 11/1974 | Buell | |
| 3,860,003 A | 1/1975 | Buell | |
| 3,929,135 A | 12/1975 | Thompson | |
| 4,315,508 A | 2/1982 | Bolick | |
| 4,324,246 A | 4/1982 | Mullane et al. | |
| 4,342,314 A | 8/1982 | Radel et al. | |
| 4,381,781 A | 5/1983 | Sciaraffa et al. | |
| 4,463,045 A | 7/1984 | Ahr et al. | |
| 4,515,595 A | 5/1985 | Kievit et al. | |
| 4,662,875 A | 5/1987 | Hirotsu et al. | |
| 4,695,278 A | 9/1987 | Lawson | |
| 4,701,174 A | 10/1987 | Johnson | |
| 4,770,656 A | 9/1988 | Proxmire et al. | |
| 4,773,903 A * | 9/1988 | Weisman et al. | 604/368 |
| 4,795,454 A | 1/1989 | Dragoo | |
| 4,834,735 A | 5/1989 | Alemany et al. | |
| 4,846,815 A | 7/1989 | Scripps | |
| 4,850,992 A | 7/1989 | Amaral et al. | |
| 4,857,067 A | 8/1989 | Wood et al. | |
| 4,869,724 A | 9/1989 | Scripps | |
| 4,888,231 A | 12/1989 | Angstadt | |
| 4,892,536 A | 1/1990 | Desmarais et al. | |
| 4,894,060 A | 1/1990 | Nestegard | |
| 4,897,084 A * | 1/1990 | Ternstrom et al. | 604/385.27 |
| 4,909,803 A | 3/1990 | Aziz et al. | |
| 4,938,753 A | 7/1990 | Van Gompel et al. | |
| 4,940,464 A | 7/1990 | Van Gompel et al. | |
| 4,946,527 A | 8/1990 | Battrell | |
| 4,962,571 A | 10/1990 | Visser | |
| 4,990,147 A | 2/1991 | Freeland | |
| 5,006,394 A | 4/1991 | Baird | |
| 5,037,416 A | 8/1991 | Allen et al. | |
| 5,069,672 A | 12/1991 | Wippler | |
| 5,077,868 A | 1/1992 | Visser | |
| 5,092,861 A | 3/1992 | Nomura et al. | |
| 5,151,092 A | 9/1992 | Buell et al. | |
| 5,156,793 A | 10/1992 | Buell et al. | |
| 5,167,897 A | 12/1992 | Weber et al. | |
| 5,217,447 A | 6/1993 | Gagnon | |
| 5,221,274 A | 6/1993 | Buell et al. | |
| 5,246,433 A | 9/1993 | Hasse et al. | |
| 5,269,775 A | 12/1993 | Freeland et al. | |
| 5,304,162 A | 4/1994 | Kuen | |
| 5,342,338 A | 8/1994 | Roe | |
| 5,358,500 A | 10/1994 | LaVon et al. | |
| 5,366,782 A | 11/1994 | Curro et al. | |
| 5,374,262 A | 12/1994 | Keuhn et al. | |
| 5,386,595 A | 2/1995 | Kuen et al. | |
| 5,399,177 A | 3/1995 | Blaney et al. | |
| 5,405,682 A | 4/1995 | Shawyer et al. | |
| H1440 H * | 5/1995 | New et al. | 604/386 |
| 5,411,498 A | 5/1995 | Fahrenkrug et al. | |
| 5,413,849 A * | 5/1995 | Austin et al. | 442/329 |
| 5,423,789 A | 6/1995 | Kuen | |
| 5,433,826 A | 7/1995 | Glomb et al. | |
| 5,447,508 A * | 9/1995 | Numano et al. | 604/385.27 |
| 5,470,639 A | 11/1995 | Gessner et al. | |
| 5,518,801 A | 5/1996 | Chappell et al. | |
| 5,540,976 A | 7/1996 | Shawver et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,607,416 A | 3/1997 | Yamamoto et al. | |
| 5,607,537 A | 3/1997 | Johnson et al. | |
| 5,607,760 A | 3/1997 | Roe | |
| 5,609,587 A | 3/1997 | Roe | |
| 5,620,431 A | 4/1997 | LeMahieu et al. | |
| 5,622,589 A | 4/1997 | Johnson et al. | |
| 5,625,222 A | 4/1997 | Yoneda et al. | |
| 5,634,917 A | 6/1997 | Fujioka et al. | |
| 5,635,191 A | 6/1997 | Roe et al. | |
| 5,635,290 A | 6/1997 | Stopper et al. | |
| 5,643,242 A | 7/1997 | LaVon et al. | |
| 5,643,588 A | 7/1997 | Roe et al. | |
| 5,662,638 A | 9/1997 | Johnson et al. | |
| 5,669,897 A | 9/1997 | LaVon et al. | |
| 5,669,901 A | 9/1997 | LaFortune et al. | |
| 5,674,216 A | 10/1997 | Buell et al. | |
| 5,695,849 A | 12/1997 | Shawver et al. | |
| 5,700,256 A | 12/1997 | Yamamoto et al. | |
| 5,733,275 A * | 3/1998 | Davis et al. | 604/387 |
| 5,746,731 A * | 5/1998 | Hisada | 604/385.3 |
| 5,749,865 A | 5/1998 | Yamamoto et al. | |
| 5,772,825 A | 6/1998 | Schmitz | |
| 5,776,123 A | 7/1998 | Goerg et al. | |
| 5,779,831 A | 7/1998 | Schmitz | |
| 5,797,824 A | 8/1998 | Tracy | |
| 5,865,823 A | 2/1999 | Curro | |
| 5,873,870 A | 2/1999 | Seitz et al. | |
| 5,897,545 A | 4/1999 | Kline et al. | |
| 5,899,895 A | 5/1999 | Robles et al. | |
| 5,916,206 A | 6/1999 | Otsubo et al. | |
| 5,916,661 A | 6/1999 | Benson et al. | |
| 5,938,648 A | 8/1999 | Lavon et al. | |
| 5,941,865 A | 8/1999 | Otsubo et al. | |
| 5,944,707 A | 8/1999 | Ronn | |
| 5,947,944 A | 9/1999 | Hetzler et al. | |
| 5,952,252 A | 9/1999 | Shawver et al. | |
| 5,957,908 A | 9/1999 | Kline et al. | |
| 5,997,521 A | 12/1999 | Robles et al. | |
| 5,997,989 A | 12/1999 | Gessner et al. | |
| 6,001,460 A | 12/1999 | Morman et al. | |
| 6,004,306 A | 12/1999 | Robles et al. | |
| 6,013,065 A * | 1/2000 | Suzuki et al. | 604/385.27 |
| 6,013,589 A | 1/2000 | DeMarais et al. | |
| 6,015,764 A | 1/2000 | Mccormack et al. | |
| 6,042,673 A | 3/2000 | Johnson et al. | |
| 6,090,234 A * | 7/2000 | Barone et al. | 156/177 |
| 6,096,668 A | 8/2000 | Abuto et al. | |
| 6,103,647 A | 8/2000 | Shultz et al. | |
| 6,107,537 A | 8/2000 | Elder et al. | |
| 6,120,487 A | 9/2000 | Ashton | |
| 6,120,488 A * | 9/2000 | VanRijswijck et al. | 604/385.28 |
| 6,120,489 A | 9/2000 | Johnson et al. | |
| 6,168,585 B1 | 1/2001 | Cesco-Cancian | |
| 6,179,820 B1 | 1/2001 | Fernfors | |
| 6,210,387 B1 * | 4/2001 | Rudberg et al. | 604/385.27 |
| 6,225,243 B1 | 5/2001 | Austin | |
| 6,264,641 B1 | 7/2001 | Van Gompel et al. | |
| 6,306,121 B1 | 10/2001 | Damaghi et al. | |
| 6,313,372 B1 | 11/2001 | Suzuki | |
| 6,364,863 B1 | 4/2002 | Yamamoto et al. | |
| 6,383,431 B1 | 5/2002 | Dobrin et al. | |
| 6,413,249 B1 | 7/2002 | Turi et al. | |
| 6,423,043 B1 | 7/2002 | Gustafsson | |
| 6,432,098 B1 | 8/2002 | Kline et al. | |
| 6,448,467 B1 | 9/2002 | Herrlein et al. | |
| 6,465,073 B1 | 10/2002 | Morman et al. | |
| 6,479,154 B1 | 11/2002 | Walton et al. | |
| 6,482,191 B1 | 11/2002 | Roe et al. | |
| 6,503,236 B1 | 1/2003 | Uitenbroek et al. | |
| 6,520,947 B1 * | 2/2003 | Tilly et al. | 604/391 |
| 6,547,774 B2 | 4/2003 | Ono et al. | |
| 6,579,274 B1 | 6/2003 | Morman et al. | |
| 6,585,713 B1 | 7/2003 | LeMahieu et al. | |
| 6,595,975 B2 | 7/2003 | Vogt et al. | |
| 6,616,648 B2 | 9/2003 | Hermansson et al. | |
| 6,623,468 B2 | 9/2003 | Shimoe | |
| 6,623,837 B2 | 9/2003 | Morman et al. | |
| 6,627,564 B1 | 9/2003 | Morman et al. | |
| 6,632,211 B2 | 10/2003 | Otsubo | |
| 6,641,568 B2 | 11/2003 | Ashton et al. | |
| 6,677,258 B2 | 1/2004 | Carroll et al. | |
| 6,680,265 B1 | 1/2004 | Smith et al. | |
| 6,680,422 B2 | 1/2004 | Roe | |
| 6,726,792 B1 | 4/2004 | Johnson et al. | |
| 6,811,865 B2 | 11/2004 | Morman et al. | |

| | | |
|---|---|---|
| 6,811,871 B2 | 11/2004 | Sen et al. |
| 6,849,324 B2 | 2/2005 | Meece et al. |
| 6,875,710 B2 | 4/2005 | Eaton et al. |
| 6,896,843 B2 | 5/2005 | Topolkaraev et al. |
| 6,909,028 B1 | 6/2005 | Shawver et al. |
| 6,942,894 B2 | 9/2005 | Alberg et al. |
| 6,955,668 B2 * | 10/2005 | Almberg et al. ............ 604/392 |
| 7,013,941 B2 | 3/2006 | Schneider et al. |
| 7,066,921 B2 | 6/2006 | Schmoker et al. |
| 7,083,604 B2 * | 8/2006 | Sakaguchi .................. 604/396 |
| 7,087,287 B2 | 8/2006 | Curro et al. |
| 7,094,227 B2 | 8/2006 | Ishiguro et al. |
| 7,122,022 B2 | 10/2006 | Drevik |
| 7,344,526 B2 * | 3/2008 | Yang et al. ................. 604/393 |
| 2001/0023341 A1 | 9/2001 | Karami |
| 2001/0041879 A1 | 11/2001 | Karami et al. |
| 2001/0042584 A1 | 11/2001 | Karami et al. |
| 2002/0007164 A1 | 1/2002 | Boggs et al. |
| 2002/0010455 A1 | 1/2002 | Hermansson et al. |
| 2002/0045879 A1 | 4/2002 | Karami |
| 2002/0095132 A1 * | 7/2002 | Ashton et al. ............... 604/392 |
| 2002/0111598 A1 | 8/2002 | Vogt et al. |
| 2002/0138065 A1 | 9/2002 | Yeater |
| 2002/0151858 A1 | 10/2002 | Karami et al. |
| 2003/0018316 A1 * | 1/2003 | Kusibojoska et al. ....... 604/392 |
| 2003/0021951 A1 | 1/2003 | Desai et al. |
| 2003/0078558 A1 | 4/2003 | Karami et al. |
| 2003/0084996 A1 | 5/2003 | Alberg et al. |
| 2003/0087059 A1 | 5/2003 | Jackson et al. |
| 2003/0087098 A1 | 5/2003 | Eaton et al. |
| 2003/0088220 A1 | 5/2003 | Molander et al. |
| 2003/0088228 A1 | 5/2003 | Desai et al. |
| 2003/0091807 A1 | 5/2003 | Desai et al. |
| 2003/0109842 A1 | 6/2003 | Louis et al. |
| 2003/0144645 A1 | 7/2003 | Karami |
| 2003/0162458 A1 | 8/2003 | Tsujiyama et al. |
| 2003/0220626 A1 | 11/2003 | Karami |
| 2003/0225382 A1 | 12/2003 | Tombult Meyer et al. |
| 2003/0233082 A1 | 12/2003 | Kline et al. |
| 2004/0006326 A1 | 1/2004 | Nakajima et al. |
| 2004/0082933 A1 | 4/2004 | Karami |
| 2004/0110442 A1 | 6/2004 | Rhim et al. |
| 2004/0121687 A1 | 6/2004 | Morman et al. |
| 2004/0121690 A1 | 6/2004 | Mleziva |
| 2004/0132374 A1 | 7/2004 | Kobayashi |
| 2004/0153043 A1 | 8/2004 | Sugito et al. |
| 2004/0167486 A1 | 8/2004 | Busam et al. |
| 2004/0186453 A1 * | 9/2004 | Shimada et al. ......... 604/385.27 |
| 2004/0193133 A1 | 9/2004 | Desai et al. |
| 2004/0193134 A1 | 9/2004 | Mueller et al. |
| 2004/0222553 A1 | 11/2004 | Desai et al. |
| 2005/0096624 A1 | 5/2005 | Hashino et al. |
| 2005/0106980 A1 | 5/2005 | Abed et al. |
| 2005/0124952 A1 | 6/2005 | Zehner et al. |
| 2005/0125879 A1 * | 6/2005 | Yang et al. ..................... 2/228 |
| 2005/0130544 A1 | 6/2005 | Cheng et al. |
| 2005/0131365 A1 * | 6/2005 | Sakaguchi ................... 604/367 |
| 2005/0154366 A1 | 7/2005 | Karami et al. |
| 2005/0164586 A1 | 7/2005 | Autran et al. |
| 2005/0165173 A1 | 7/2005 | Autran et al. |
| 2005/0211368 A1 | 9/2005 | McGuire et al. |
| 2005/0214461 A1 | 9/2005 | Desai et al. |
| 2005/0215964 A1 | 9/2005 | Autran et al. |
| 2006/0047260 A1 * | 3/2006 | Ashton et al. ................. 604/396 |
| 2006/0141883 A1 | 6/2006 | Nishiguchi et al. |
| 2006/0247598 A1 * | 11/2006 | Roehrl et al. ................. 604/392 |
| 2007/0066954 A1 * | 3/2007 | LaVon et al. ................. 604/392 |
| 2007/0287983 A1 * | 12/2007 | Lodge et al. ................. 604/402 |
| 2008/0004582 A1 * | 1/2008 | Lodge et al. ............ 604/385.01 |
| 2008/0004583 A1 * | 1/2008 | Desai et al. ............. 604/385.01 |
| 2008/0004584 A1 * | 1/2008 | Langdon et al. ........ 604/385.01 |
| 2008/0004586 A1 * | 1/2008 | Lodge et al. ............ 604/385.03 |
| 2008/0004587 A1 * | 1/2008 | Lodge et al. ............ 604/385.03 |
| 2008/0004589 A1 * | 1/2008 | Roe et al. ..................... 604/396 |
| 2008/0004590 A1 * | 1/2008 | Lodge et al. ................. 604/396 |
| 2008/0004591 A1 * | 1/2008 | Desai et al. .................. 604/396 |
| 2008/0004592 A1 * | 1/2008 | Lodge et al. ................. 604/396 |
| 2008/0004593 A1 * | 1/2008 | Lodge et al. ................. 604/401 |
| 2008/0015537 A1 * | 1/2008 | Lodge et al. ................. 604/396 |
| 2008/0027406 A1 * | 1/2008 | Shirai et al. ............. 604/385.24 |
| 2008/0125739 A1 * | 5/2008 | Lodge et al. ............ 604/385.03 |
| 2008/0188822 A1 * | 8/2008 | Lodge et al. ............ 604/385.03 |

FOREIGN PATENT DOCUMENTS

| | | |
|---|---|---|
| EP | 0 858 787 | 8/1998 |
| EP | 1350493 A1 | 10/2003 |
| EP | 1 787 610 | 5/2007 |
| GB | 243 719 | 2/1926 |
| WO | WO9409736 * | 5/1994 |
| WO | WO9516746 A1 | 6/1995 |
| WO | WO 98/48750 | 11/1998 |
| WO | WO2005065680 A1 | 7/2005 |
| WO | WO2006017518 A2 | 2/2006 |
| WO | WO2006017674 A1 | 2/2006 |
| WO | WO2006017518 A3 | 12/2006 |

OTHER PUBLICATIONS

U.S. Appl. No. 11/240,838, filed Sep. 30, 2005, Kline, et al.
U.S. Appl. No. 11/329,796, filed Jan. 11, 2006, Dziezok, et al.
U.S. Appl. No. 11/329,797, filed Jan. 11, 2006, Dziezok, et al.
U.S. Appl. No. 11/361,918, filed Feb. 24, 2006, Anderson, et al.
U.S. Appl. No. 11/599,829, filed Jun. 7, 2006, Autran, et al.
U.S. Appl. No. 11/599,862, filed Nov. 15, 2006, Lodge, et al.
U.S. Appl. No. 60/811,700, filed Jun. 7, 2006, Roe, et al.
U.S. Appl. No. 11/859,852, filed Nov. 15, 2006, Roe, et al.
PCT Search Report, mailed Nov. 21, 2007, 4 pages.
U.S. Appl. No. 11/077,779, filed Mar. 11, 2005, Donald Carroll Roe, et al.

* cited by examiner

DISPOSABLE WEARABLE ABSORBENT ARTICLES WITH ANCHORING SYSTEMS

CROSS REFERENCE TO RELATED APPLICATIONS

This application claims the benefit of U.S. Provisional Application No. 60/811,580, filed Jun. 7, 2006, which is hereby incorporated by reference.

FIELD OF THE INVENTION

In general, embodiments of the present disclosure relate to disposable wearable absorbent articles. In particular, embodiments of the present disclosure relate to disposable wearable absorbent articles with anchoring systems.

BACKGROUND OF THE INVENTION

Disposable wearable absorbent articles include disposable diapers and disposable incontinence undergarments. A disposable wearable absorbent article can receive and contain bodily waste while being worn by a wearer. Such articles can be made with various materials in a number of configurations. For example, a disposable wearable absorbent article can be made with a stretchable waistband and a non-stretchable outer cover. The design of a disposable wearable absorbent article can affect the way that the article fits on a wearer. Unfortunately, some disposable wearable absorbent articles fit wearers poorly.

As an example, some disposable wearable absorbent articles with stretchable waistbands and non-stretchable outers cover can have a bulky form on a wearer. A disposable wearable absorbent article that has a bulky form can feel uncomfortable and look unattractive. Also as an example, some disposable wearable absorbent articles with stretchable waistbands and non-stretchable outer covers can resist conforming to a wearer's body as the wearer moves. A disposable wearable absorbent article that resists conforming to a wearer's body can feel uncomfortable and look unattractive. As a further example, some disposable wearable absorbent articles with a stretchable waistband and a non-stretchable outer cover can sag or slip down on a wearer. A disposable wearable absorbent article that sags or slips down on a wearer can feel uncomfortable, look unattractive, and perform poorly as the article tends to leak.

BRIEF DESCRIPTION OF THE INVENTION

DETAILED DESCRIPTION OF THE INVENTION

Figure 1A:
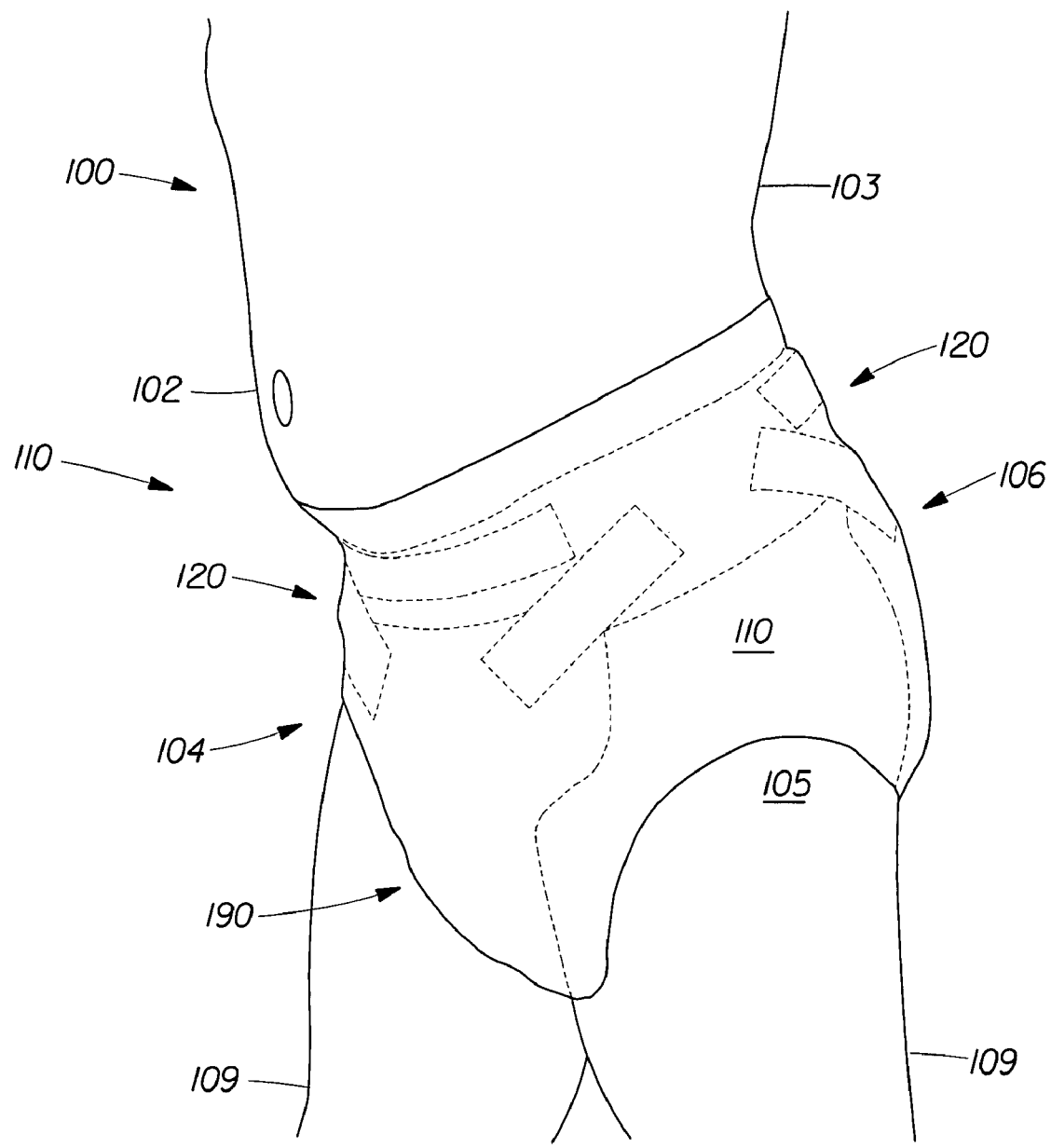
FIG. 1A illustrates a perspective view of an embodiment of a disposable wearable absorbent article with an anchoring system and an absorbent core, as worn on a wearer, according to the present disclosure.

Embodiments of the present disclosure include disposable wearable absorbent articles with anchoring systems that fit wearers well. In some embodiments, these articles can include stretchable outer covers. The designs of these disposable wearable absorbent articles allow the articles to have an underwear-like appearance that conforms to a wearer's body as the wearer moves. The designs of these articles also help prevent the articles from sagging or slipping down on a wearer. As a result, the disposable wearable absorbent articles of the present disclosure can feel comfortable, look attractive, and perform well as the articles tend to fit snugly, stay in place, and not leak.

Embodiments of the present disclosure include disposable wearable absorbent articles. Throughout the present disclosure, the term "disposable wearable absorbent article" refers to an article, configured to be worn on a lower torso of a human body of a wearer, configured to receive and contain bodily exudates (e.g., urine and feces) from the body, and configured to be disposed of after a single use by the wearer. Thus, a disposable wearable absorbent article is configured such that the soiled article, or a soiled portion of the article, is not intended to be restored and reused (e.g., not intended to be laundered). Examples of disposable wearable absorbent articles include disposable diapers, disposable incontinence undergarments, etc. A disposable wearable absorbent article can be configured in various ways, such a pant-type configuration with a pre-formed waist opening and leg openings and a fastenable configuration with means for a consumer to fasten the article around a body of a wearer.

In embodiments of the present disclosure, a disposable wearable absorbent article can include an absorbent core. Throughout the present disclosure, the term "absorbent core" refers to a part of a disposable wearable absorbent article configured to absorb bodily exudates received into the article from a body of a wearer. An absorbent core can be configured in various ways, as will be understood by one of ordinary skill in the art. Examples of absorbent cores include absorbent core assemblies (with one or more optional core structures), bucket-shaped absorbent cores, removable and/or replaceable absorbent cores, etc.

In embodiments of the present disclosure, a disposable wearable absorbent article with an anchoring system, as described herein, can include a stretchable outer cover. For example, the outer cover can be a uniaxially stretchable outer cover, configured to stretch in one direction. Also as an example, the outer cover can be a biaxially stretchable outer cover, configured to stretch in two directions. In various embodiments, the outer cover can be configured as described in US non-provisional patent application entitled "Biaxially Stretchable Outer Cover for an Absorbent Article," filed on Nov. 15, 2006 with Express Mail No. EV916939625 and further identified by Ser. No. 11/599,829, which is hereby incorporated by reference.

In embodiments of the present disclosure, a disposable wearable absorbent article with an anchoring system, as described herein, can include an outer cover configured in various ways, including configurations of part or all of the outer cover as stretchable, non-stretchable, with an elastic nonwoven, with an elastic film and extensible nonwoven, with an extensible film and an elastic nonwoven, pre-stretched with elastic strands allowed to contract, mechanically activated, with zero strain laminate, and/or combinations of these and any other outer cover configurations. In various embodiments of the present disclosure, a disposable wearable absorbent article with an anchoring system, as described herein, can include a printed outer cover forming one or more elements of an anchoring system separately or in combination with various basis weights, chemistries, and/or mechanical activations, as will be understood by one of ordinary skill in the art.

In embodiments of the present disclosure, a disposable wearable absorbent article with an anchoring system, as described herein, can be configured with various structures and/or functions as described in US non-provisional patent application entitled "Absorbent Article Having an Anchored Core Assembly," filed on Nov. 15, 2006 with Express Mail No. EV916939634 and further identified by Ser. No. 11/599,862, which is hereby incorporated by reference. Also, in embodiments of the present disclosure, a disposable wearable absorbent article with an anchoring system, as described herein, can have a wrap and tuck configuration as described in US non-provisional patent application entitled "Disposable Absorbent Article Having a Wrap and Tuck Configuration," filed on Nov. 15, 2006 with Express Mail No. EV916939617, and further identified by Ser. No. 11/599,852, which is hereby incorporated by reference.

Throughout the present disclosure, various figures illustrate human bodies. As a whole, these figures are intended to illustrate the presence of various external human anatomical features and general relationships between these features. For ease of reference, the present disclosure refers to many of these features using simple and informal terminology. These human anatomical features can relate to disposable wearable absorbent articles with anchoring systems, according to embodiments of the present disclosure. Some figures are intended to illustrate how such articles can fit on human bodies.

In the present disclosure, figures that illustrate human bodies are not intended to illustrate all human anatomical features. These figures are also not intended to teach precise details or exact proportions of the human anatomical features that are illustrated. Further, these figures are not intended to limit embodiments of the present disclosure to any particular size, shape, or type of human body.

When a disposable wearable absorbent article is placed on a wearer, the article is placed in an initial position with respect to the wearer. The location of this initial position can depend on a number of factors, such as the size of the article, the shape of the wearer's body, and the manner in which the article is placed on the wearer. For example, an initial position of a fastenable diaper can depend in part on a location at which the diaper is fastened around a wearer. However, as a disposable wearable absorbent article is worn by a wearer, a number of forces can act upon the article.

Some of these forces can tend to move the article on the wearer. Throughout the present disclosure, the term "load" refers to a force that tends to move an article out of place on a wearer. First, a disposable wearable absorbent article can experience various loads from placement of the article on a wearer. As an example, some pretension forces from fastening the article can drive the article downward. Second, a disposable wearable absorbent article can experience various loads from the article's environment. A wearer's clothes can pull on the article, for example. Third, a disposable wearable absorbent article can experience various loads from a wearer's movements. For example, as a wearer changes positions or moves about the wearer's body can push against parts of the article or create dynamic forces in the article. Fourth, the force of gravity can move a disposable wearable absorbent article down on a wearer. The article can experience a significant load from the force of gravity, due to a mass of the article as well as a mass of any bodily waste contained in the article. These loads, can act upon a disposable wearable absorbent article, tending to move the article on a wearer.

However, other forces acting upon a disposable wearable absorbent article can tend to hold the article in place on a wearer. First, a disposable wearable absorbent article can experience various holding forces from placement of the article on a wearer. As an example, other pretension forces from fastening the article can drive the article upward. Second, parts of a disposable wearable absorbent article can experience friction forces from contact with a wearer's skin. For example, the article can experience a friction force where a waistband of the article wraps around and against the wearer's waist. Third, parts of a disposable wearable absorbent article can experience reaction forces from contact with various external anatomical features on a wearer's body. As an example, the article can experience reaction forces where the article contacts protruding portions of the wearer's hips. In this example, the reaction forces react against the force of gravity by pushing up on the article. These holding forces can act upon a disposable wearable absorbent article, tending to hold the article in place on a wearer.

As some forces tend to move a disposable wearable absorbent article down on a wearer and other forces tend to hold the article up on the wearer, part or all of the article may or may not move, depending on whether or not such forces are balanced. If the forces tending to hold the article up can equal the forces tending to move the article down, then the article can hold in place on the wearer. If the forces tending to move the article down are greater than the forces tending to hold the article up, then part or all of the article can move down on the wearer. Sometimes, forces can move down part or all of disposable wearable absorbent article, resulting in sagging and/or slipping.

However, embodiments of the present disclosure can help prevent disposable wearable absorbent articles from sagging or slipping down on a wearer. A disposable wearable absorbent article can include an anchoring system. In various embodiments, an anchoring system can be configured to collect at least some of the loads acting upon the article. The anchoring system can also be configured to anchor itself to a body of a wearer. In this way, the anchoring system can balance the collected loads with holding forces obtained from the anchoring. By balancing the collected loads with the obtained holding forces, the anchoring system can at least assist in holding the disposable wearable absorbent article in place on a wearer.

An anchoring system in a disposable wearable absorbent article can be configured in various ways to collect at least some of the loads acting upon the article. In some embodiments, an anchoring system can be configured to carry loads from an absorbent core of the article. For example, an anchoring system can include one or more elements that can be joined to the absorbent core in various ways, as described herein. In order for an anchoring system to collect loads effectively, a disposable wearable absorbent article can be configured so that the anchoring system tends to collect loads and other parts of the article tend to not collect loads. Thus, loads can be directed through the anchoring system, instead of being distributed through other parts of the article, such as the outer cover.

Parts of a disposable wearable absorbent article can be configured in various ways such that the parts tend to not collect loads. Force-decoupling can be used in some of these configurations. Throughout the present disclosure, the term "force-decoupled" refers to a configured relationship between parts of a disposable wearable absorbent article. Where a first part is force-decoupled from a second part, the parts are configured such that neither part tends to transmit a substantial force to the other, while the article is worn by a wearer. A disposable wearable absorbent article can include an absorbent core and an outer cover, wherein the outer cover can be substantially force decoupled from the absorbent core, as described in various embodiments herein.

Force-decoupling does not necessarily preclude the force-decoupled parts from being directly connected, so long as substantial force is not transmitted between the parts through that direct connection, while the article is worn by a wearer. Force transmissions from direct connections in a disposable wearable absorbent article can be substantially reduced in various ways, such as configurations of pathway lengths and/or material extensibilities. As an example embodiment, in a disposable wearable absorbent article with an absorbent core directly connected to an outer cover at a first point and directly connected to an anchoring system at a second point, the article can be configured such that a pathway from the first point through the absorbent core to the second point is shorter than a pathway from the first point through the outer cover to the second point.

The functionality of this example can be explained with the following pathway length illustration. Ends of a first rope are connected to a first point and a second point. Similarly, ends of a second rope are also connected to the first point and the second point. The two ropes are similar except that one rope is quite a bit shorter than the other. The first point and the second point are close enough to each other that the middle of each of the ropes hangs down. If the first point moves away from the second point, then the middles of both of the ropes begin to rise up from their hanging positions. However, the shorter rope will draw taut before the longer rope draws taut. The shorter rope will form a straight line between the first point and the second point while the middle of the longer rope is still hanging down somewhat. Thus, the shorter rope will carry the tension from a force that is moving the points apart. While the longer rope is still connected to the first point and the second point, it will not carry that tension.

This pathway length illustration can be used to explain the prior example embodiment with the disposable wearable absorbent article. The pathway from the first point through the absorbent core to the second point is like the shorter rope in the pathway length illustration. The pathway from the first point through the outer cover to the second point is like the longer rope in the pathway length illustration. As a result, the disposable wearable absorbent article is configured such that a load from the absorbent core causes tension through the absorbent core (shorter pathway) before it causes tension through the outer cover (longer pathway). The tension through the absorbent core can transmit through the second point to the anchoring system. Thus, in the example configuration, a load from the absorbent core can cause tension in the anchoring system before it causes tension in the outer cover.

Force transmissions from direct connections in a disposable wearable absorbent article can also be substantially reduced through configurations of material extensibilities. As an example embodiment, in a disposable wearable absorbent article with an absorbent core joined to an anchoring system and directly connected to an outer cover, the outer cover can be configured to be stretchable while the absorbent core can be configured to be non-stretchable.

The functionality of this example can be explained with the following material extensibilities illustration. Ends of an extension spring are connected to a first point and a second point. Similarly, ends of a rope are also connected to the first point and the second point. The extension spring forms a straight line between the first point and the second point, while the middle of the rope is hanging down somewhat. If the first point moves away from the second point, then the extension spring will begin to extend and the middle of the rope will begin to rise up from its hanging position. However, the rope may draw taut while the extension spring is still extending. Thus, the rope may carry more of the tension from a force that is moving the points apart. While the extension spring is still connected to the first point and the second point and extended between the points, it may carry less of that tension.

This materials extensibilities illustration can be used to explain the prior example embodiment with the disposable wearable absorbent article. The stretchable outer cover is like the extension spring in the materials extensibilities illustration. The non-stretchable absorbent core is like the rope in the materials extensibilities illustration. As a result, the disposable wearable absorbent article is configured such that a load from the absorbent core causes greater tension in the (non-stretchable) absorbent core and lesser tension in the (stretchable) outer cover. The greater tension through the absorbent core can transmit to the anchoring system. Thus, in the example configuration, a load from the absorbent core can cause greater tension in the anchoring system than in the outer cover.

In various embodiments, a first portion of an element in a disposable wearable absorbent article can be force-decoupled from a second portion of that same element. For example, an interior portion of an outer cover can be force-decoupled from an outer perimeter of that same outer cover. This can be accomplished by configuring differing material extensibilities within the outer cover. As examples, the interior portion of the outer cover can be configured with a lower extensibility and an exterior portion of the outer cover, between the interior portion and the perimeter, can be configured with a higher extensibility, or vice versa. In this way, the higher extensibility configuration in the exterior portion can force-decouple the interior portion of the outer cover from the outer perimeter of the outer cover.

As described above, an anchoring system can be configured to collect loads acting upon a disposable wearable absorbent article, to anchor itself to a body of a wearer, and to balance the collected loads with holding forces obtained from the anchoring. Throughout the present disclosure, the term "anchored" refers to a configured relationship between part or all of an anchoring system in a disposable wearable absorbent article and part or all of a body of a wearer, while the article is worn by the wearer. Where an element of an anchoring system is anchored to a portion of a body of a wearer, at least part of the element is in contact with the portion of the body and the anchoring system is configured to at least reduce and/or prevent relative movement between the element and the portion, while the article is worn by the wearer.

An anchoring system can be anchored to a body of a wearer with one or more elements of the anchoring system configured to contact various parts of a body of a wearer. For example, an anchoring system can be at least partially anchored by wrapping one or more anchoring system elements at least partway around a front, back, and/or side of a body of a wearer, thus creating friction and/or reaction forces. A part of the body with a relatively smaller radius of curvature can, in some embodiments, provide greater friction forces, since an element can tend to wrap around such parts more tightly. Also as an example, an anchoring system can be at least partially anchored by setting one or more anchoring system elements on, around, and/or above protruding portions of a body of a wearer, thus creating friction and/or reaction forces. A part of the body with a relatively larger horizontal protrusion can, in some embodiments, provide greater reaction forces, since an element can tend to hang and/or ride on such parts more securely. In various embodiments, parts of a body of wearer to which an anchoring system can be anchored, can be referred to as anchoring zones.

In order to collect loads, anchor itself to a body of a wearer, and balance various forces, an anchoring system can be configured to include a number of anchoring system elements. In some embodiments, an anchoring system element can be an elongated element configured to carry tension. Anchoring system elements can follow various pathways on external surfaces of a body of a wearer of the disposable wearable absorbent article in which the anchoring system is included. The shapes of these external surfaces can affect the shapes of the pathways. The shapes of the pathways can, in turn, affect configurations of anchoring system elements. Many external surfaces on human bodies include curved shapes, such as a curve around a hip of a human body. In some embodiments, an anchoring system element that follows a curved pathway can be a geodesic.

The term geodesic relates to a theoretical element with mathematical properties described by curved geometries. In this theoretical context, a geodesic is a curved line on a curved surface, wherein the curved line appears to travel straight, without turning to the left or to the right, when viewed from that curved surface. In other words, a geodesic can be thought of as a line pulled taut on a frictionless curved surface. On a flat surface, the shortest distance between two points is a straight line. On a curved surface, the shortest distance between two points is a geodesic. Throughout the present disclosure a geodesic with two endpoints that does not intersect itself is referred to as an "open geodesic." Throughout the present disclosure a geodesic that intersects itself is referred to as a "closed" geodesic and the point of intersection is referred to as a "corner."

An anchoring system element can be configured as a geodesic as the element follows various curved pathways on external surfaces of a body of a wearer. An anchoring system element that is loaded in tension (e.g., axial loading) is a geodesic, since the tension conforms the element to the curved pathway. When a point load is added to an anchoring system element that is a geodesic, at an angle other than in-line with the geodesic, that point load deforms the geodesic, creating two new geodesics in the anchoring system element. When an anchoring system element that is a geodesic is subjected to a load distributed along at least a portion of the length of the element, at an angle other than in-line with the geodesic, the element no longer behaves as a geodesic, and instead begins to act in a manner referred to herein as "geometric anchoring."

An anchoring system can include a number of anchoring system elements, some of which can be configured as geodesics. A circumferential anchoring member (CAM) is an anchoring system element that is a physical tension carrying pathway on part or all of a closed path on a curved surface of a body of a wearer. A CAM can include a number of elements, such as anchoring bands or fasteners. Part or all of a CAM can be straight, curved, angled, segmented, or combinations of these shapes. A CAM can be made from any material suitable for carrying tensions in an anchoring system. An anchoring band is an anchoring system element that is a physical band of material with a length between two ends and a defined width that is less than the length. An anchoring band can be configured to transmit force in tension from one end to the other. In various embodiments, an anchoring band can be a load distribution element. A load distribution element (LDE) is a type of anchoring band that joins an absorbent core of a disposable wearable absorbent article to an anchoring system. One or more of these elements can be used in anchoring systems of the present disclosure, as described herein.

Throughout the present disclosure, the term "joined" refers to configurations whereby an element is directly connected to another element by affixing the element directly to the other element and to configurations whereby an element is indirectly secured to another element by affixing the element to intermediate member(s) which in turn are affixed to the other element.

The embodiments of FIGS. 1A through 17 describe various anchoring systems for use in disposable wearable absorbent articles. These anchoring systems can be configured with one or more CAMs, LDEs, anchoring bands, fasteners and/or other anchoring system elements, in various ways, as described herein. Each of these anchoring systems can be configured in a disposable wearable absorbent article to anchor an absorbent core to a wearer. In various embodiments, each of these anchoring systems can be configured in a disposable wearable absorbent article to substantially force decouple an outer cover from an absorbent core. In various embodiments, each of these anchoring systems can be configured in a disposable wearable absorbent article to carry substantially all loads from an absorbent core. In various embodiments, each of these anchoring systems can be configured in a disposable wearable absorbent article to geodesically anchor the absorbent core to a wearer. In various embodiments, a disposable wearable absorbent article can be configured with each of these anchoring systems such that a load from an absorbent core causes tension in the anchoring system before it causes tension in an outer cover. In various embodiments, a disposable wearable absorbent article can be configured with each of these anchoring systems such that an absorbent core is joined to an outer cover at a first point and is joined to an anchoring system at a second point, wherein the article is further configured such that a pathway from the first point through the absorbent core to the second point is shorter than a pathway from the first point through the outer cover to the second point. In various embodiments, a disposable wearable absorbent article can be configured with each of these anchoring systems such that a load from the absorbent core causes greater tension in the anchoring system than in the outer cover.

FIG. 1A illustrates a perspective view of an embodiment of a disposable wearable absorbent article 110 with an anchoring system 120 and an absorbent core 190, as worn on a wearer 100, according to the present disclosure. The wearer 100 includes a belly 102, a back 103, hips 105, and upper legs 109. The anchoring system 120 can be configured to anchor the absorbent core 190 to the wearer 100, as described herein.

The disposable wearable absorbent article 110 includes a front 104 and a back 106. The front 104 is a portion of the disposable wearable absorbent article 110 disposed generally proximate to and/or below the belly 102 of the wearer 100, when the disposable wearable absorbent article 110 is worn by the wearer 100. A general reference to the "front" can mean the front 104, part or all of an element in the front 104, and/or a disposition in the front 104. The back 106 is a portion of the disposable wearable absorbent article 110 disposed generally proximate to and/or below the back 103 of the wearer 100, when the disposable wearable absorbent article 110 is worn by the wearer 100. A general reference to the "back" can mean the back 106, part or all of an element in the back 106, and/or a disposition in the back 106. A lateral centerline of the disposable wearable absorbent article 110 forms a boundary between the front 104 and the back 106, as described in connection with the embodiment of FIG. 1E. The front and back terminology described above is used for disposable wearable absorbent articles throughout the present disclosure unless otherwise indicated. In various embodiments, the disposable wearable absorbent article 110 can be a pant-type disposable wearable absorbent article as described in connection with the embodiment of FIG. 1E or a fastenable disposable wearable absorbent article as described in connection with the embodiment of FIG. 1F.

Figure 1B:
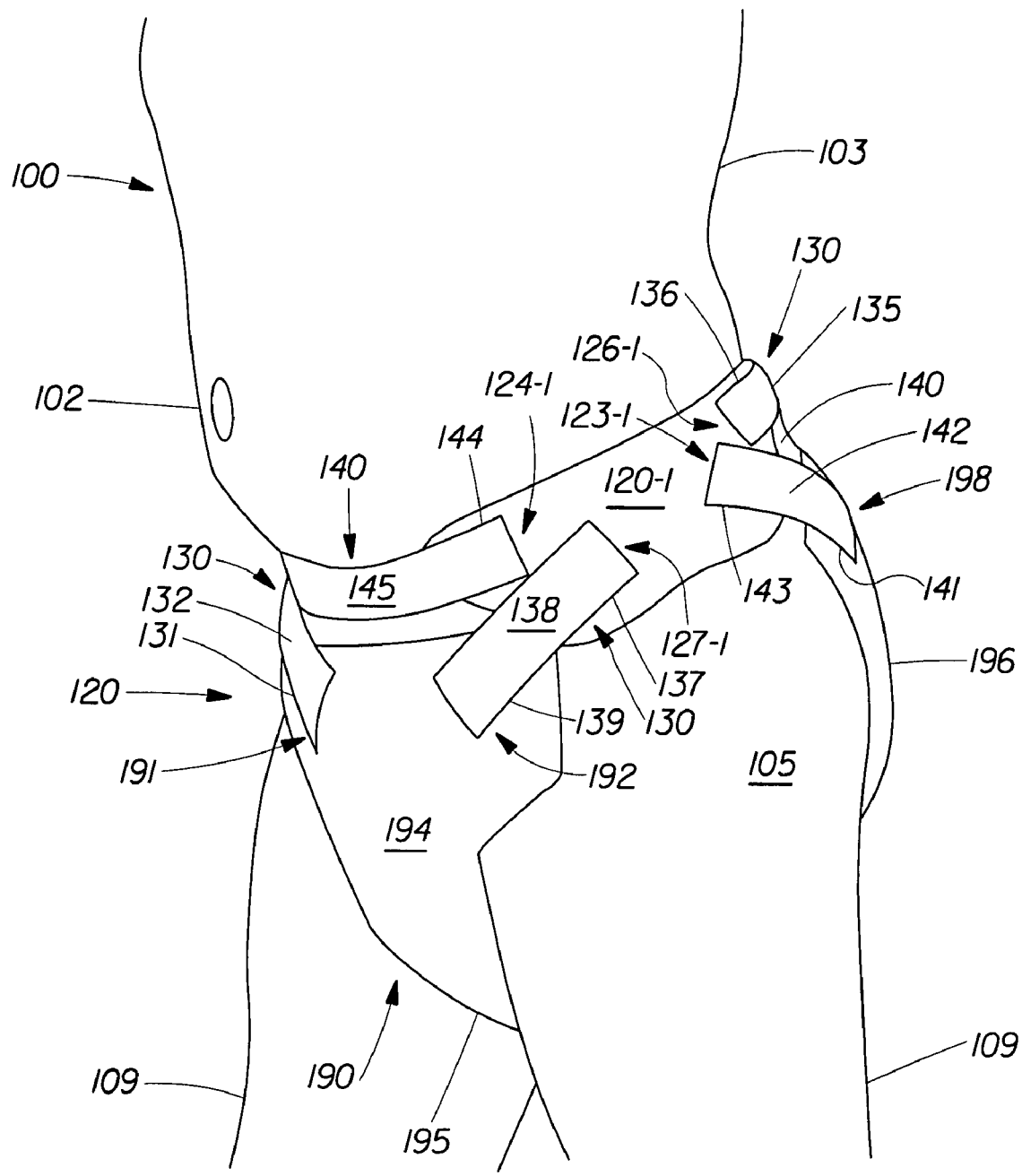
FIG. 1B illustrates a perspective view of the anchoring system and the absorbent core of the embodiment of FIG. 1A, as worn on the wearer, according to the present disclosure.

FIG. 1B illustrates a perspective view of the anchoring system 120 and the absorbent core 190 of the embodiment of FIG. 1A, as worn on the wearer 100, according to the present disclosure. The wearer 100 includes the belly 102, the back 103, the hip 105, and the upper legs 109. The absorbent core 190 includes a front portion 194 disposed in the front 104, a crotch region 195, and a back portion 196 disposed in the back 106. The anchoring system 120 includes a first CAM 130 with a first end 131 joined to the front portion 194, a first middle anchoring band 135 disposed across the back 106, and a second end 139 joined to the front portion 194. Throughout the present disclosure, unless otherwise indicated, the term "middle" refers to any portion of an element between ends of the element. The first CAM 130 includes a first end anchoring band 132 joined to a second side element joined to the first middle anchoring band 135 joined to a first side element 120-1 joined to a second end anchoring band 138. The first end 131 of the first end anchoring band 132 is directly connected to the front portion 194 at a first location 191. The first middle anchoring band 135 includes a first-side end 136, which is directly connected to the first side element 120-1 at a first side location 126-1. The second end anchoring band 138 includes a first-side end 137, which is directly connected to the first side element 120-1 at a first side location 127-1. The second end anchoring band 138 also includes the second end 139, which is directly connected to the front portion 194 at a second location 192. In the embodiment of FIG. 1B, the second location 192 is laterally spaced apart from the first location 191.

The anchoring system 120 also includes a second CAM 140 with a third end 141 joined to the back portion 196, a second middle anchoring band 145 disposed across the front 104, and a fourth end joined to the back portion 196. The second CAM 140 includes a third end anchoring band 142 joined to the first side element 120-1 joined to the second middle anchoring band 145 joined to the second side element joined to a fourth end anchoring band. The third end anchoring band 142 includes a third end 141, which is directly connected to the back portion 196 at a third location 198. The third end anchoring band 142 also includes a first-side end 143, which is directly connected to the first side element 120-1 at a first side location 123-1. The second middle anchoring band 145 includes a first-side end 144, which is directly connected to the first side element 120-1 at a first side location 124-1.

Figure 1C:
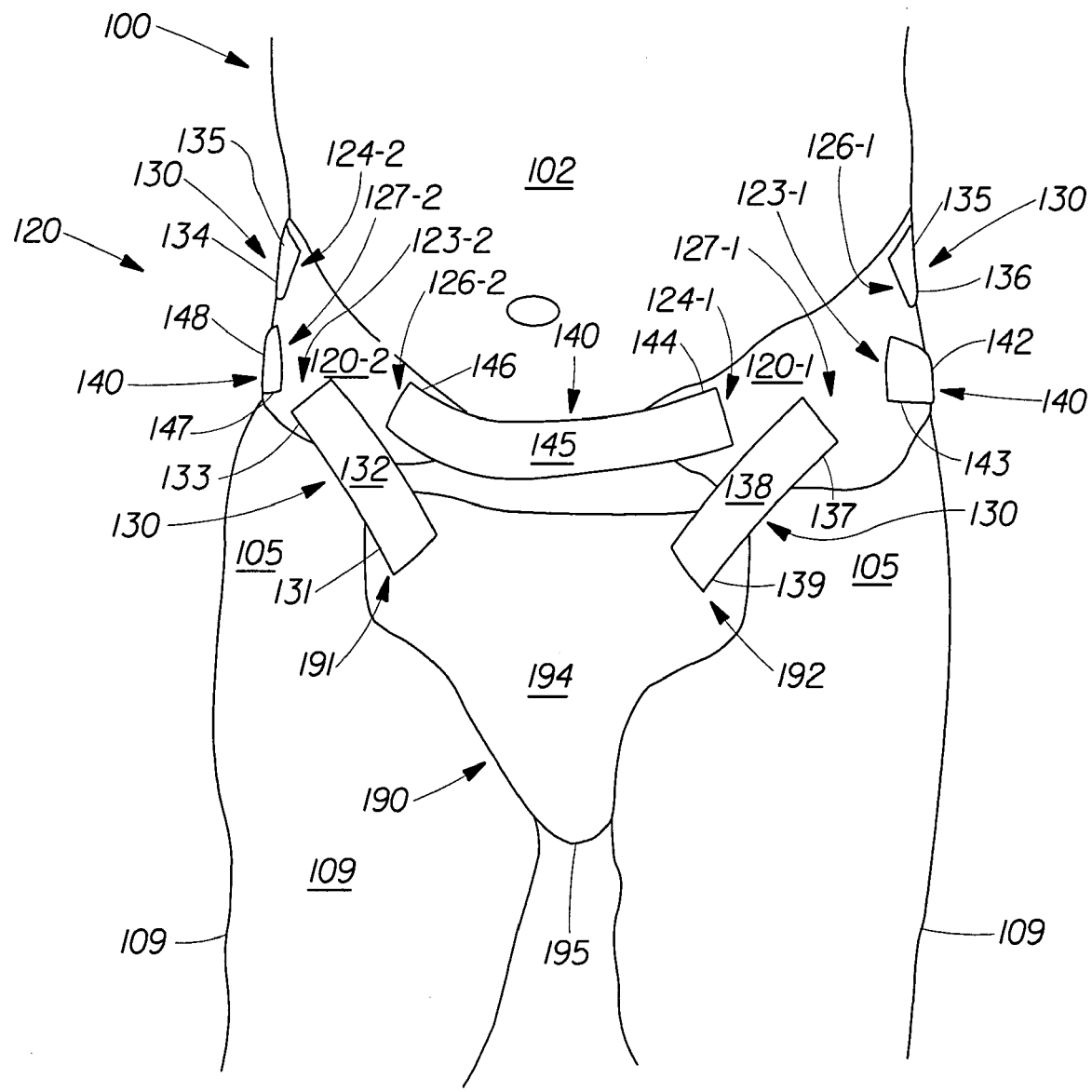
FIG. 1C illustrates a front view of the anchoring system and the absorbent core of the embodiment of FIG. 1A, as worn on the wearer, according to the present disclosure.

FIG. 1C illustrates a front view of the anchoring system 120 and the absorbent core 190 of the embodiment of FIG. 1A, as worn on the wearer 100, according to the present disclosure. The wearer 100 includes the belly 102, the hips 105, and the upper legs 109. The absorbent core 190 includes the front portion 194 and the crotch region 195. The anchoring system 120 includes the first CAM 130. The first CAM 130 includes the first end anchoring band 132 joined to the second side element 120-2 joined to the first middle anchoring band 135 joined to the first side element 120-1 joined to the second end anchoring band 138. The first end anchoring band 132 includes the first end 131 directly connected to the front portion 194 at the first location 191 and the second-side end 133 directly connected to the second side element 120-2 at a second side location 123-2. The first middle anchoring band 135 includes a second-side end 134 directly connected to the second side 120-2 at a second side location 124-2 and the first-side end 136 directly connected to the first side element 120-1 at the first side location 126-1. The second end anchoring band 138 includes the first-side end 137 directly connected to the first side element 120-1 at the first side location 127-1 and the second end 139 directly connected to the front portion 194 at the second location 192. In the embodiment of FIG. 1C, the second location 192 is laterally spaced apart from the first location 191.

The anchoring system 120 also includes the second CAM 140. The second CAM 140 includes a third end anchoring band 142 joined to the first side element 120-1 joined to the second middle anchoring band 145 joined to the second side element 120-2 joined to the fourth end anchoring band 148. The third end anchoring band 142 includes a first-side end 143, which is directly connected to the first side element 120-1 at the first side location 123-1. The second middle anchoring band 145 includes the first-side end 144 directly connected to the first side element 120-1 at the first side location 124-1 and a second-side end 146 directly connected to the second side element 120-2 at the second side location 126-2. The fourth end anchoring band 148 includes a second-side end 147, which is directly connected to the second side element 120-2 at the second side location 127-2.

Figure 1D:
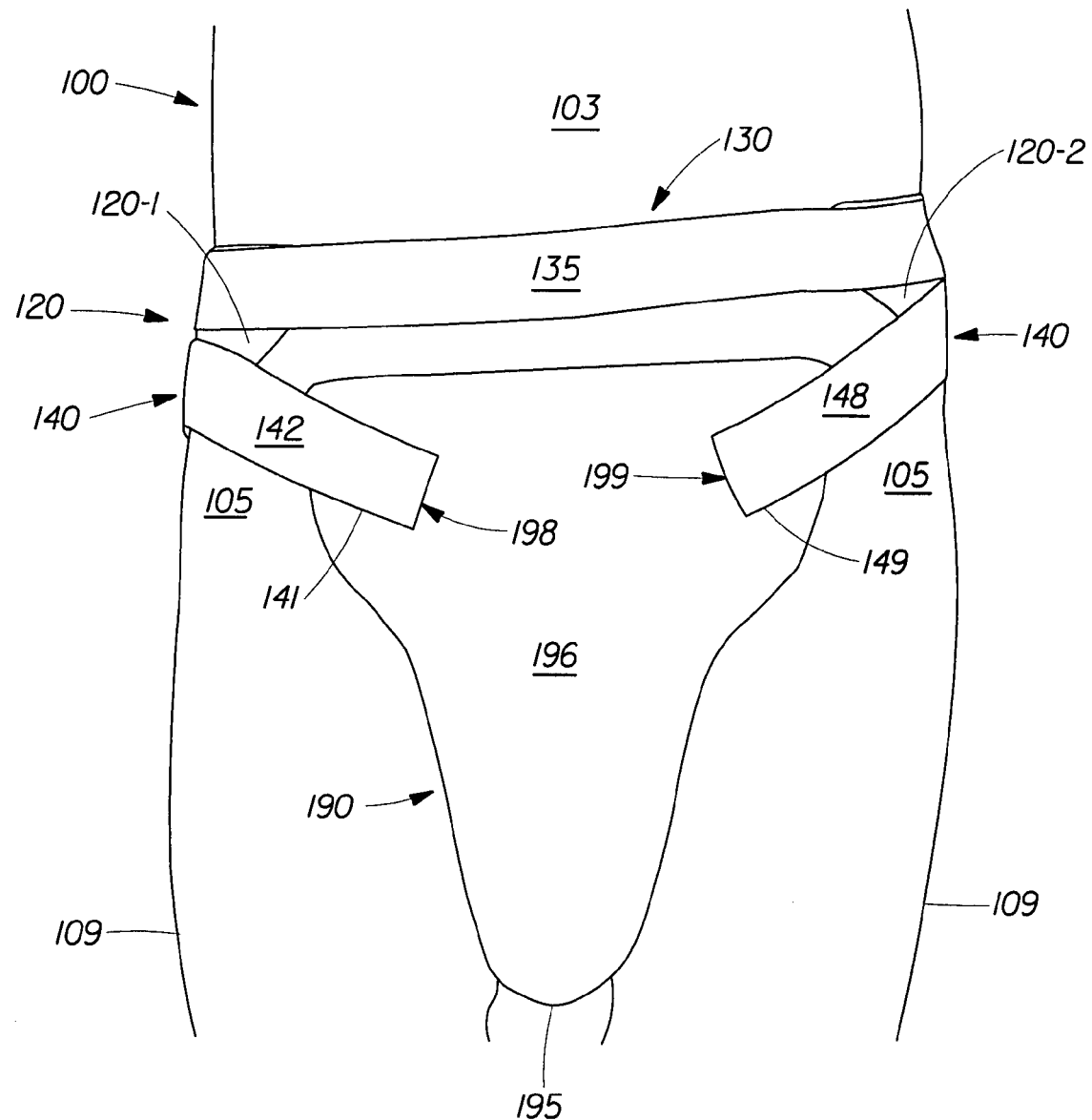
FIG. 1D illustrates a back view of the anchoring system and the absorbent core of the embodiment of FIG. 1A, as worn on the wearer, according to the present disclosure.

FIG. 1D illustrates a back view of the anchoring system 120 and the absorbent core 190 of the embodiment of FIG. 1A, as worn on the wearer 100, according to the present disclosure. The wearer 100 includes the back 103, the hips 105, and the upper legs 109. The absorbent core 190 includes the crotch region 195 and the back portion 196. The anchoring system 120 includes the first CAM 130 and the second CAM 140. The first CAM 130 includes the second side element 120-2 joined to the first middle anchoring band 135 joined to the first side element 120-1. The second CAM 140 includes the third end anchoring band 142 joined to the first side element 120-1 and the second side element 120-2 joined to the fourth end anchoring band 148. The third end anchoring band 142 includes the third end 141, which is directly connected to the back portion 196 at the third location 198. The fourth end anchoring band 148 includes the fourth end 149, which is directly connected to the back portion 196 at the fourth location 199. In the embodiment of FIG. 1D, the fourth location 199 is laterally spaced apart from the third location 198.

Figure 1E:
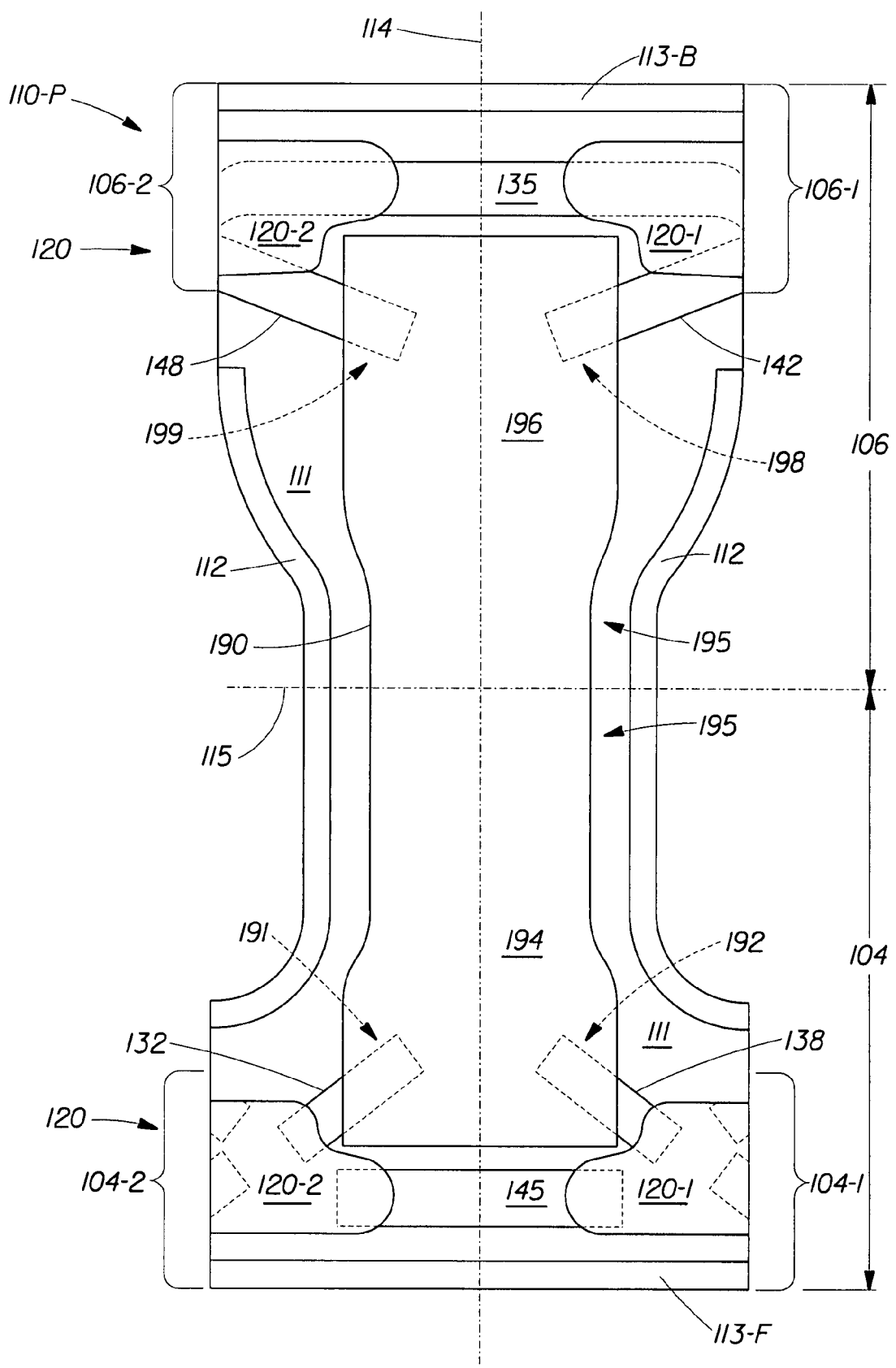
FIG. 1E illustrates a plan view of the disposable wearable absorbent article of the embodiment of FIG. 1A, as a pant-type disposable wearable absorbent article, according to the present disclosure.

FIG. 1E illustrates a plan view of the disposable wearable absorbent article 110 of the embodiment of FIG. 1A, as a pant-type disposable wearable absorbent article 110-P, according to the present disclosure. The pant-type disposable wearable absorbent article 110-P includes the front 104 with a first front side interface 104-1 and a second front side interface 104-2 and the back 106 with a first back side interface 106-1 and a second back side interface 106-2. The first front side interface 104-1 and the first back side interface 106-1 can be joined to form a first side interface between the front 104 and the back 106. The second front side interface 104-2 and the second back side interface 106-2 can also be joined to form a second side interface between the front 104 and the back 106. Thus, the first and second side interfaces can each carry tension for the first CAM 130 and/or the second CAM 140 between the front 104 and the back 106.

The pant-type disposable wearable absorbent article 110-P also includes a chassis 111, leg bands 112, a waistband with a front portion of the waistband 113-F and a back portion of the waistband 113-B, a longitudinal centerline 114, and a lateral centerline 115. The lateral centerline 115 forms a boundary between the front 104 and the back 106 in the pant-type disposable wearable absorbent article 110-P. The longitudinal centerline 114 and the lateral centerline 115 also provide lines of reference for referring to relative locations of parts of the pant-type disposable wearable absorbent article 110-P. When a first part is nearer to the longitudinal centerline 114 than a second part, the first part can be considered laterally inboard to the second part. Similarly, the second part can be considered laterally outboard from the first part. When a third part is nearer to the lateral centerline 115 than a fourth part, the third part can be considered longitudinally inboard to the fourth part. Similarly, the fourth part can be considered longitudinally outboard from the third part. This lateral and longitudinal terminology is used for disposable wearable absorbent articles throughout the present disclosure unless otherwise indicated.

The pant-type disposable wearable absorbent article 110-P includes the absorbent core 190 with the front portion 194 disposed in the front 104, the crotch region 195 disposed generally around the lateral centerline 115, and the back portion 196 disposed in the back 106. The anchoring system 120 is joined to the absorbent core 190.

The anchoring system 120 includes the first CAM 130 and the second CAM 140. The first CAM 130 includes the first end anchoring band 132 joined to the second side element 120-2, through the second side interface, joined to the first middle anchoring band 135 joined to the first side element 120-1, through the first side interface, joined to the second end anchoring band 138. The first CAM 130 is directly connected to the front portion 194 at the first location 191 and the second location 192. The second CAM 140 includes the third end anchoring band 142 joined to the first side element 120-1, through the first side interface, joined to the second middle anchoring band 145 joined to the second side element 120-2, through the second side interface, joined to the fourth end anchoring band 148. The second CAM 140 is directly connected to the back portion 196 at the third location 198 and the fourth location 199.

In the embodiment of FIG. 1E, the first CAM 130 and the second CAM 140 each include the first side element 120-1, which is divided by the first front side interface 104-1 and the first back side interface 106-1, and the second side element 120-2, which is divided by the second front side interface 104-2 and the second back side interface 106-2. However, in various embodiments, an anchoring system can be included in a pant-type disposable wearable absorbent article in a number of ways. For example, a pant-type disposable wearable absorbent article can include one or more anchoring system elements divided by side interfaces disposed further laterally inboard and/or outboard than the side interfaces in the embodiment of FIG. 1E. Also as an example, a pant-type disposable wearable absorbent article can include one or more anchoring system elements configured to extend beyond a side interface and into a corresponding front and/or back when the interfaces are joined. As an additional example, one or more anchoring system elements can be configured in side panels, which can be joined to the front and to the back on each side of a pant-type disposable wearable absorbent article. As a further example, one or anchoring system elements can be added to a pant-type disposable wearable absorbent article after side interfaces are joined, so that those anchoring system elements need not be divided by the side interfaces.

Figure 1F:
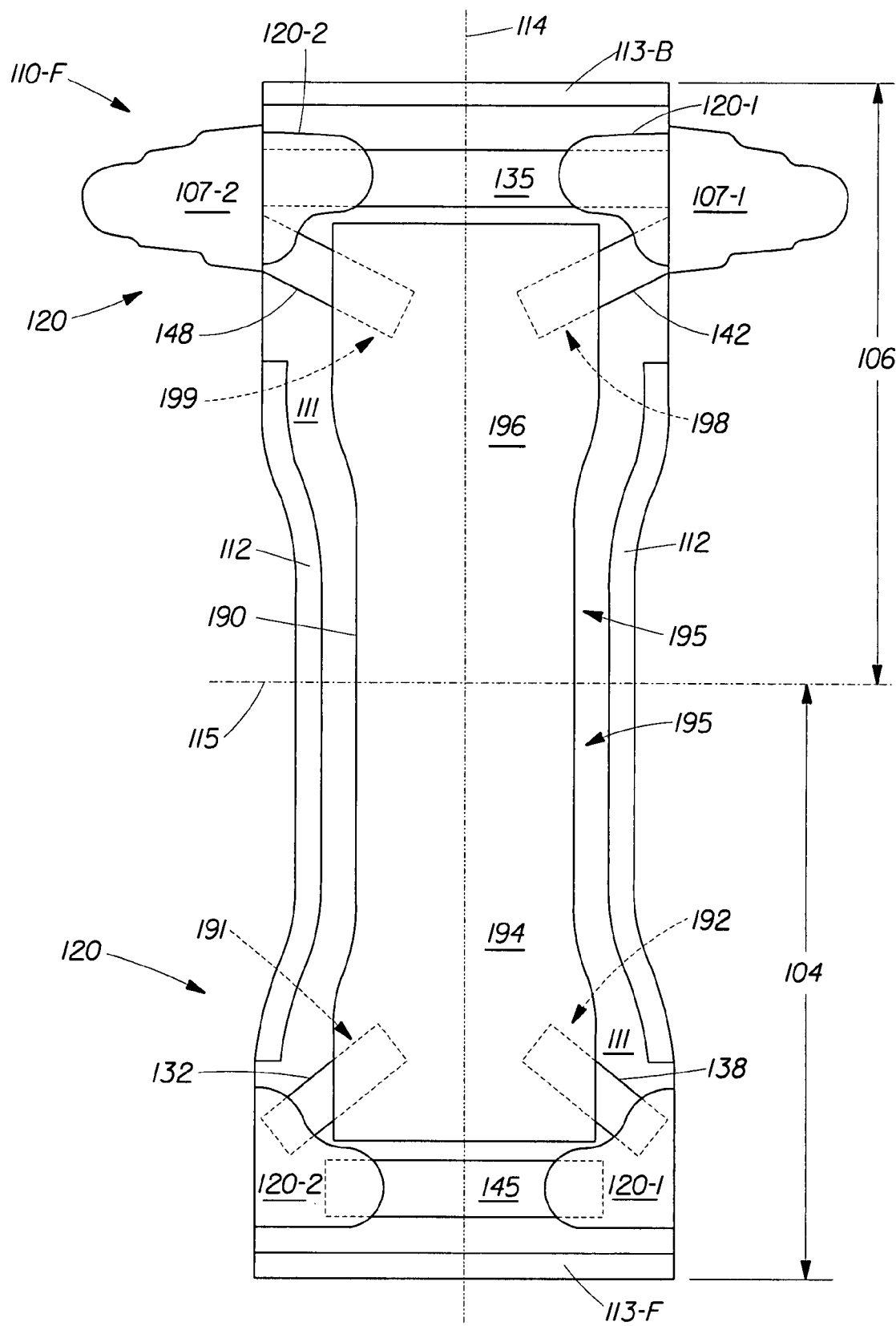
FIG. 1F illustrates a plan view of the disposable wearable absorbent article of the embodiment of FIG. 1A, as a fastenable disposable wearable absorbent article, according to the present disclosure.

FIG. 1F illustrates a plan view of the disposable wearable absorbent article of the embodiment of FIG. 1A, as a fastenable disposable wearable absorbent article 110-F, according to the present disclosure. The fastenable disposable wearable absorbent article 110-F includes the front 104 and the back 106 with a first side ear 107-1 and a second side ear 107-2. The first side ear 107-1 and the second side ear 106-1 can each be fastened to the front 104 to fasten the fastenable disposable wearable absorbent article 110-F. Thus, when fastened, the first and second side ears 107-1 and 107-2 can each carry tension for the first CAM 130 and/or the second CAM 140 between the front 104 and the back 106. Such side ears can be configured to fasten to the front at locations which properly carry such tension, as will be understood by one of ordinary skill in the art. In the embodiment of FIG. 1F, the first side ear 107-1 can be configured to fasten to the front 104 at a location laterally outboard from a point at which the second end anchoring band 138 is joined to the first side element 120-1, in order to properly carry tension from the first side ear 107-1 to the second end anchoring band 138. Similarly, the second side ear 107-1 can be configured to fasten to the front 104 at a location laterally outboard from a point at which the first end anchoring band 132 is joined to the second side element 120-2, in order to properly carry tension from the second side ear 107-2 to the first end anchoring band 132. In various embodiments, a fastenable disposable wearable absorbent article with an anchoring system can be fastened in a number of ways, as will be understood by one of ordinary skill in the art. In an alternative embodiment, a side ear can be configured to carry tension in a CAM between the front and the back by configured overlapping of elements under tension, through use of a normal force against a body of a wearer of the disposable wearable absorbent article, as will be understood by one of ordinary skill in the art.

The fastenable disposable wearable absorbent article 110-F also includes a chassis 111, leg bands 112, a waistband with a front portion of the waistband 113-F and a back portion of the waistband 113-B, a longitudinal centerline 114, and a lateral centerline 115. The lateral centerline 115 forms a boundary between the front 104 and the back 106 in the fastenable disposable wearable absorbent article 110-F. The fastenable disposable wearable absorbent article 110-F includes the absorbent core 190 with the front portion 194 disposed in the front 104, the crotch region 195 disposed generally around the lateral centerline 115, and the back portion 196 disposed in the back 106. The anchoring system 120 is joined to the absorbent core 190.

The anchoring system 120 includes the first CAM 130 and the second CAM 140. In the embodiment of FIG. 1F, the first CAM 130 and the second CAM 140 each include the first side element 120-1, which is divided into a front portion of the first side element 120-1 and a back portion of the first side element 120-1. The first CAM 130 and the second CAM 140 also each include the second side element 120-2, which is divided into a front portion of the second side element 120-2 and a back portion of the second side element 120-2.

The first CAM 130 includes the first end anchoring band 132 joined to the front portion of the second side element 120-2 fastened to the second side ear 107-2 joined to the back portion of the second side element 120-2 joined to the first middle anchoring band 135 joined to the back portion of the first side element 120-1 joined to the first side ear 107-1 joined to the front portion of the first side element 120-1 joined to the second end anchoring band 138. The first CAM 130 is directly connected to the front portion 194 at the first location 191 and the second location 192.

The second CAM 140 includes the third end anchoring band 142 joined to the back portion of the first side element 120-1 joined to the first side ear 107-1 fastened to the front portion of the first side element 120-1 joined to second first middle anchoring band 145 joined to the front portion of the second side element 120-2 joined to the second side ear 107-2 joined to the back portion of the second side element 120-2 joined to the fourth end anchoring band 148. The second CAM 140 is directly connected to the back portion 196 at the third location 198 and the fourth location 199.

In the embodiment of FIG. 1F, the first CAM 130 and the second CAM 140 each include the first side ear 107-1 and the second side ear 107-2 as intermediate to the divided portions of the first side element 120-1 and the second side element 120-2. However, in various embodiments, an anchoring system can be included in a fastenable disposable wearable absorbent article in a number of ways, as will be understood by one of ordinary skill in the art.

Figure 2B:
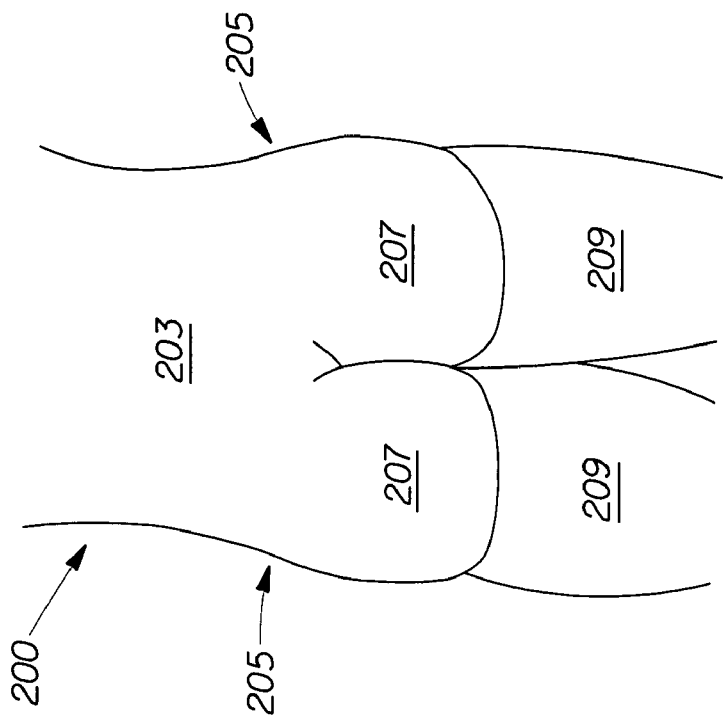
FIG. 2B illustrates a back view of the portion of the human body of the embodiment of FIG. 2A.
Figure 2A:
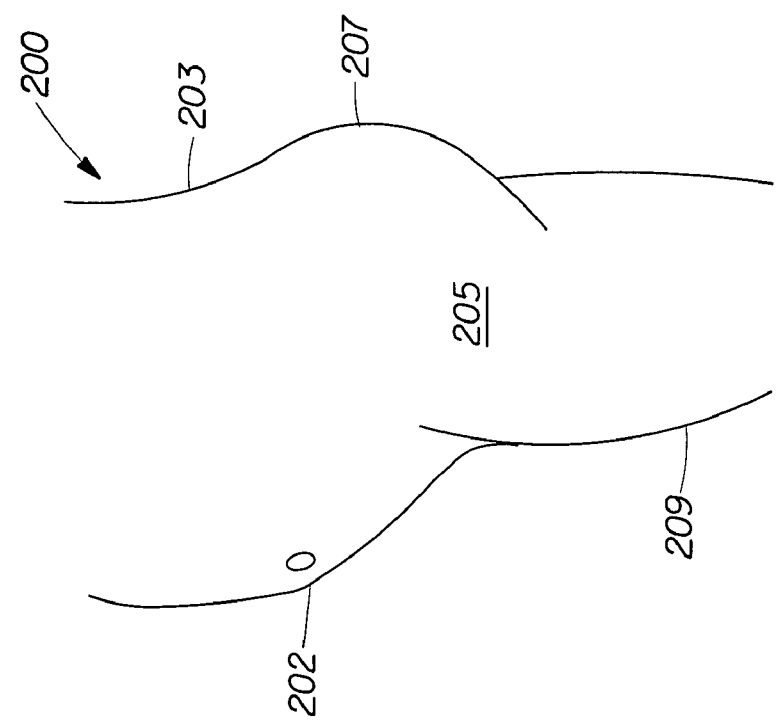
FIG. 2A illustrates a side view of a portion of a human body.

FIG. 2A illustrates a side view of a portion of a human body 200. The human body 200 includes a belly 202, a back 203, hips 205, buttocks 207, and upper legs 209. The features of the human body 200 illustrate how embodiments of disposable wearable absorbent articles of the present disclosure can fit on bodies of wearers. The features of the human body 200 also illustrate various parts of a human body to which embodiments of anchoring systems of the present disclosure can be anchored.

FIG. 2B illustrates a back view of the portion of the human body 200 of the embodiment of FIG. 2A. The human body 200 includes the back 203, the hips 205, the buttocks 207, and the upper legs 209.

Figure 3A:
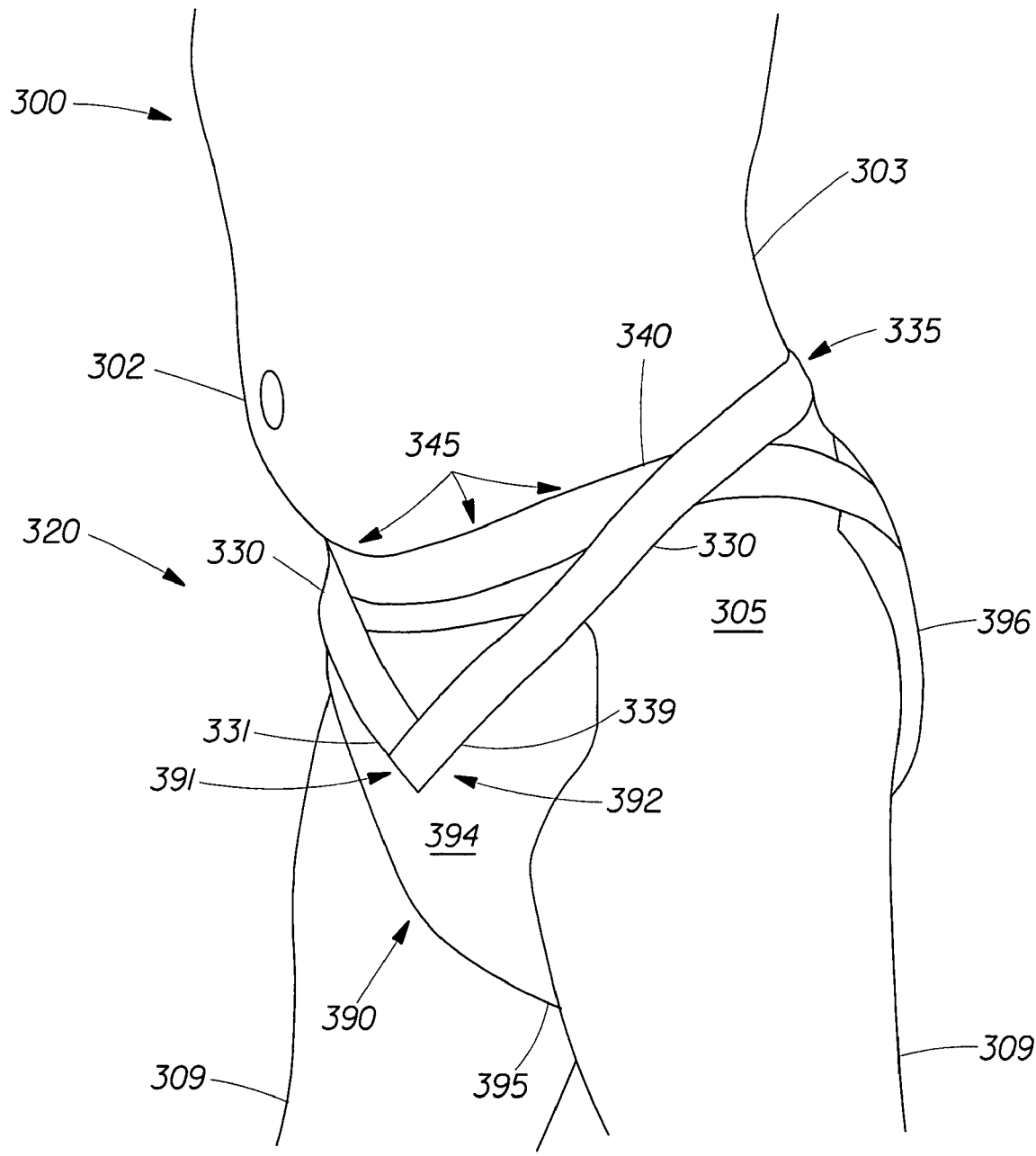
FIG. 3A illustrates a perspective view of an embodiment of an anchoring system and an absorbent core for use in a disposable wearable absorbent article, as worn on a wearer, according to the present disclosure.

FIG. 3A illustrates a perspective view of an embodiment of an anchoring system 320 and an absorbent core 390 for use in a disposable wearable absorbent article, as worn on a wearer 300, according to the present disclosure. The wearer 300 includes a belly 302, a back 303, a hip 305, and upper legs 309. The anchoring system 320 is joined to the absorbent core 390. The anchoring system 320 is configured for use in a disposable wearable absorbent article with a front and back, as described herein. The absorbent core 390 includes a front portion 394 disposed in the front, a crotch region 395, and a back portion 396 disposed in the back. The anchoring system 320 includes a first CAM 330 with a first end 331 joined to the front portion 394, a first middle 335 disposed across the back, and a second end 339 joined to the front portion 394. The first end 331 is directly connected to the front portion 394 at a first location 391 and the second end 339 is directly connected to the front portion 394 at a second location 392 that at least partially overlaps the first location 391. The anchoring system 320 also includes a second CAM 340 with a third end joined to the back portion 396, a second middle 345 disposed across the front, and a fourth end joined to the back portion 396. The third end is directly connected to the back portion 396 at a third location. The fourth end is directly connected to the back portion 396 at a fourth location that at least partially overlaps the third location. In various embodiments, the anchoring system 320 can alternatively include a second CAM configured with the back portion 396 as described in connection with a second CAM 440 of the embodiment of FIG. 4, a second CAM 540 of the embodiment of FIG. 5, or a second CAM 640 of the embodiment of FIG. 6, as will be understood by one of ordinary skill in the art.

In some embodiments, the first CAM 330 and the second CAM 340 of the anchoring system 320 can each be configured as closed geodesics. The first CAM 330 can be considered a closed geodesic as it wraps around a portion of a body of the wearer 300 and intersects itself at a corner formed by the first location 391 and the second location 392. The second CAM 340 can also be considered a closed geodesic as it wraps around a portion of a body of the wearer 300 and intersects itself at a corner in the back, in a manner similar to the first CAM 330. As a result, the anchoring system 320 can be configured to geodesically anchor the absorbent core 390 to the wearer 300. Similarly, CAMs in the anchoring system embodiments of FIGS. 1A-1F, 4-6, 13, and 14, can also be configured as closed geodesics, as will be understood by one of ordinary skill in the art.

Figure 3B:
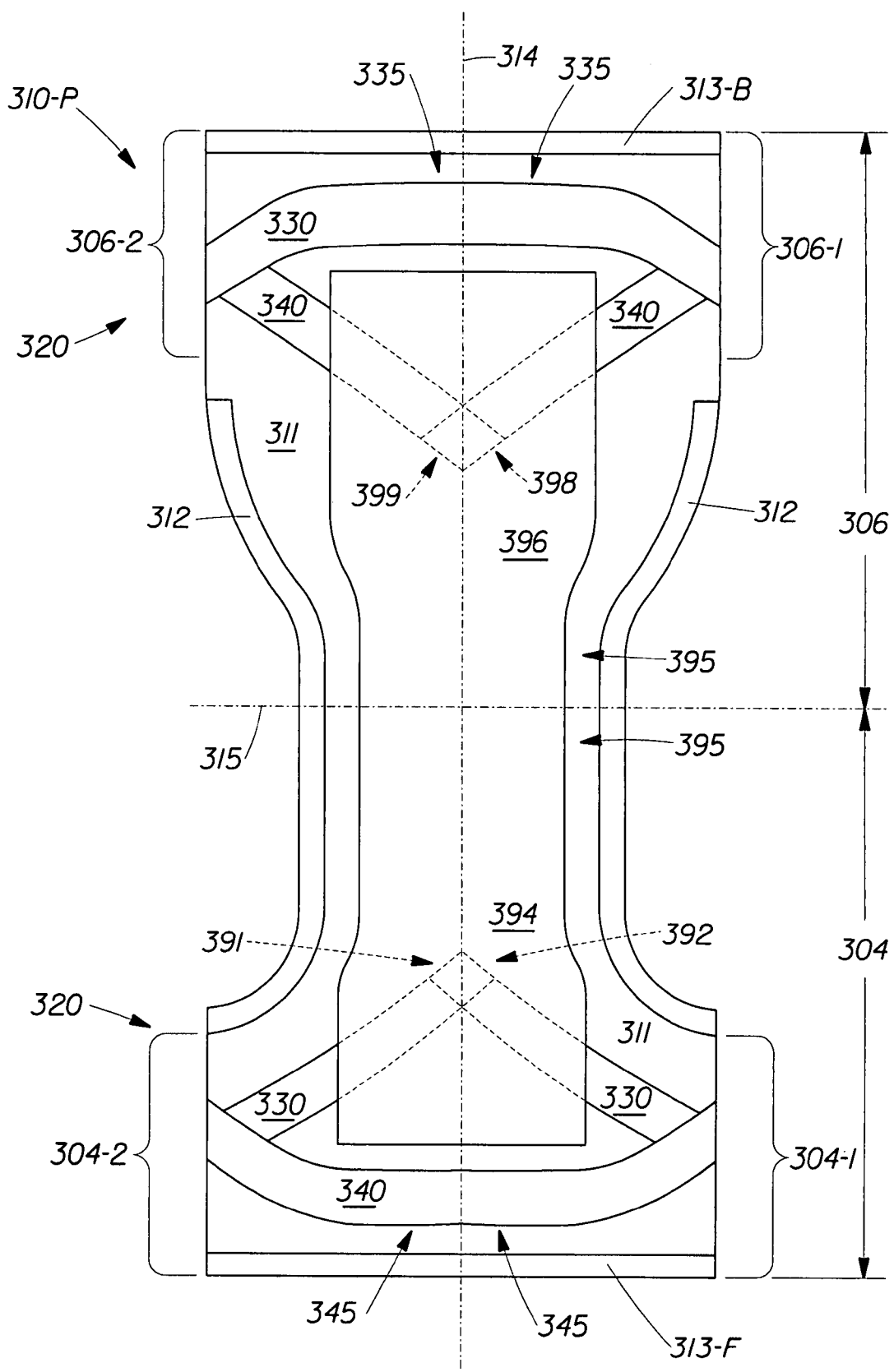
FIG. 3B illustrates a plan view of an embodiment of a pant-type disposable wearable absorbent article including the anchoring system of the embodiment of FIG. 3A, according to the present disclosure.

FIG. 3B illustrates a plan view of an embodiment of a pant-type disposable wearable absorbent article 310-P including the anchoring system 320 of the embodiment of FIG. 3A, according to the present disclosure. The pant-type disposable wearable absorbent article 310-P includes a front 304 with a first front side interface 304-1 and a second front side interface 304-2 and a back 306 with a first back side interface 306-1 and a second back side interface 306-2. The first front side interface 304-1 and the first back side interface 306-1 can be joined to form a first side interface between the front 304 and the back 306. The second front side interface 304-2 and the second back side interface 306-2 can also be joined to form a second side interface between the front 304 and the back 306. Thus, the first and second side interfaces can each carry tension for the first CAM 330 and/or the second CAM 340 between the front 304 and the back 306.

The pant-type disposable wearable absorbent article 310-P also includes a chassis 311, leg bands 312, a waistband with a front portion of the waistband 313-F and a back portion of the waistband 313-B, a longitudinal centerline 314, and a lateral centerline 315. The lateral centerline 315 forms a boundary between the front 304 and the back 306 in the pant-type disposable wearable absorbent article 310-P. The pant-type disposable wearable absorbent article 310-P includes the absorbent core 390 with the front portion 394 disposed in the front 304, the crotch region 395 disposed generally around the lateral centerline 315, and the back portion 396 disposed in the back 306. The anchoring system 320 is joined to the absorbent core 390.

The anchoring system 320 includes the first CAM 330 with the first end joined to the front portion 394, the first middle 335 disposed through the second side interface across the back 306 and through the first side interface, and the second end joined to the front portion 394. The first end is directly connected to the front portion 394 at the first location 391 and the second end is directly connected to the front portion 394 at the second location 392 that at least partially overlaps the first location 391. The anchoring system 320 also includes the second CAM 340 with the third end joined to the back portion 396, the second middle 345 through disposed the first side interface across the front 304 and through the second side interface, and the fourth end joined to the back portion 396. The third end is directly connected to the back portion 396 at the third location 398 and the fourth end is directly connected to the back portion 396 at the fourth location 399 that at least partially overlaps the third location 398.

Figure 4:
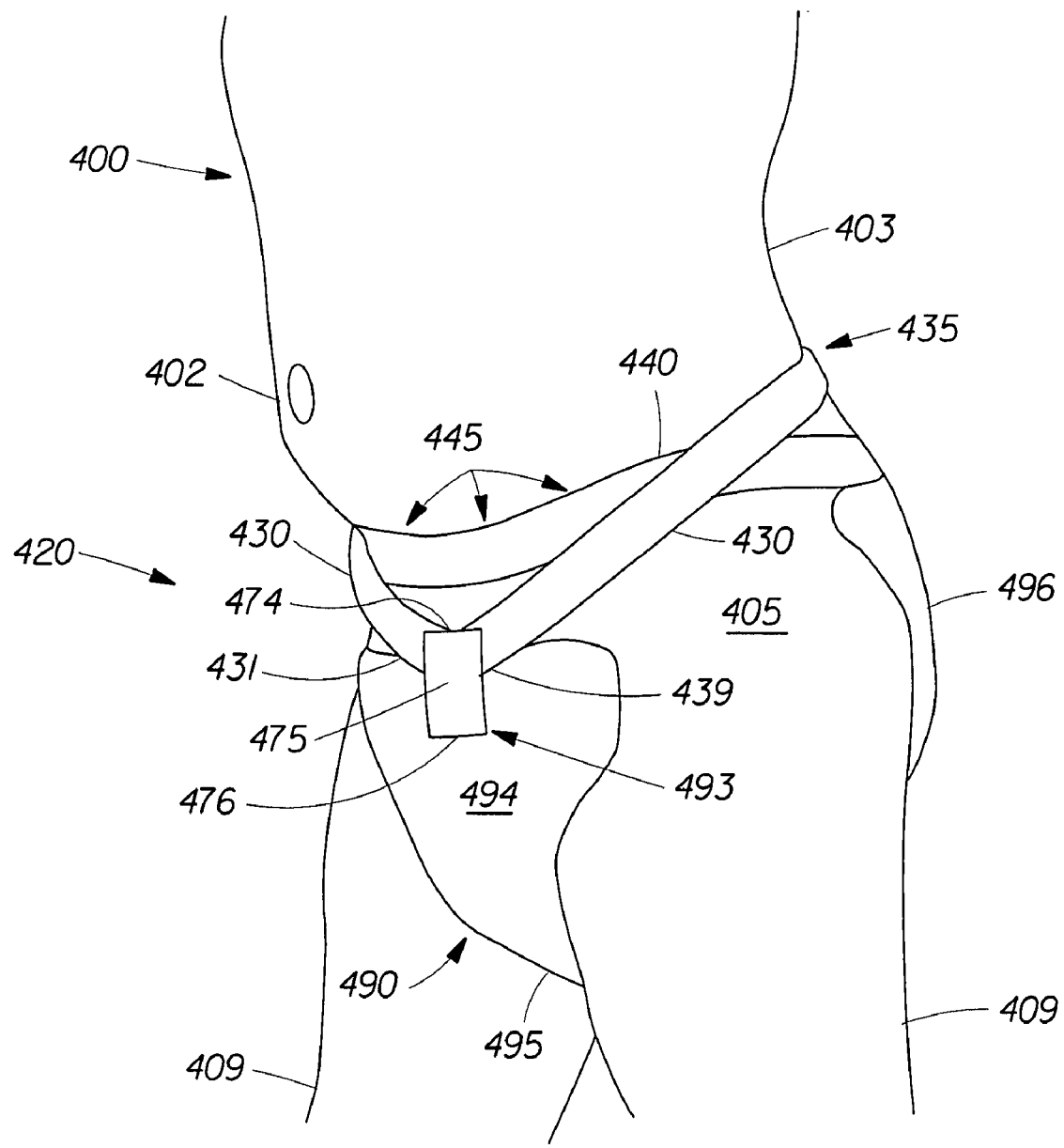
FIG. 4 illustrates a perspective view of an embodiment of an anchoring system and an absorbent core for use in a disposable wearable absorbent article, as worn on a wearer, according to the present disclosure.

FIG. 4 illustrates a perspective view of an embodiment of an anchoring system 420 and an absorbent core 490 for use in a disposable wearable absorbent article, as worn on a wearer 400, according to the present disclosure. The wearer 400 includes a belly 402, a back 403, a hip 405, and upper legs 409. The anchoring system 420 is joined to the absorbent core 490. The anchoring system 420 is configured for use in a disposable wearable absorbent article with a front and back, as described herein. The absorbent core 490 includes a front portion 494 disposed in the front, a crotch region 495, and a back portion 496 disposed in the back. The anchoring system 420 includes a first CAM 430 with a first end 431 joined to the front portion 494, a first middle 435 disposed across the back, and a second end 439 joined to the front portion 494. The anchoring system 420 also includes a front LDE 475 with front LDE ends 474 and 476. The first end 431 and the second end 439 are each joined to the front LDE 475 at the front LDE end 474. The front LDE end 476 of the front LDE 475 is directly connected to the front portion 494 at a front LDE location 493.

The anchoring system 420 also includes a second CAM 440 with a third end joined to the back portion 496, a second middle 445 disposed across the front, and a fourth end joined to the back portion 496. The anchoring system 420 also includes a back LDE. The third end and the fourth end are each joined to the back LDE and the back LDE is directly connected to the back portion 496. In various embodiments of the anchoring system 420, more or fewer LDEs can be used. In various embodiments, the anchoring system 420 can alternatively include a second CAM configured with the back portion 496 as described in connection with the second CAM 340 of the embodiment of FIGS. 3A and 3B, the second CAM 540 of the embodiment of FIG. 5, or the second CAM 640 of the embodiment of FIG. 6, as will be understood by one of ordinary skill in the art.

Figure 5:
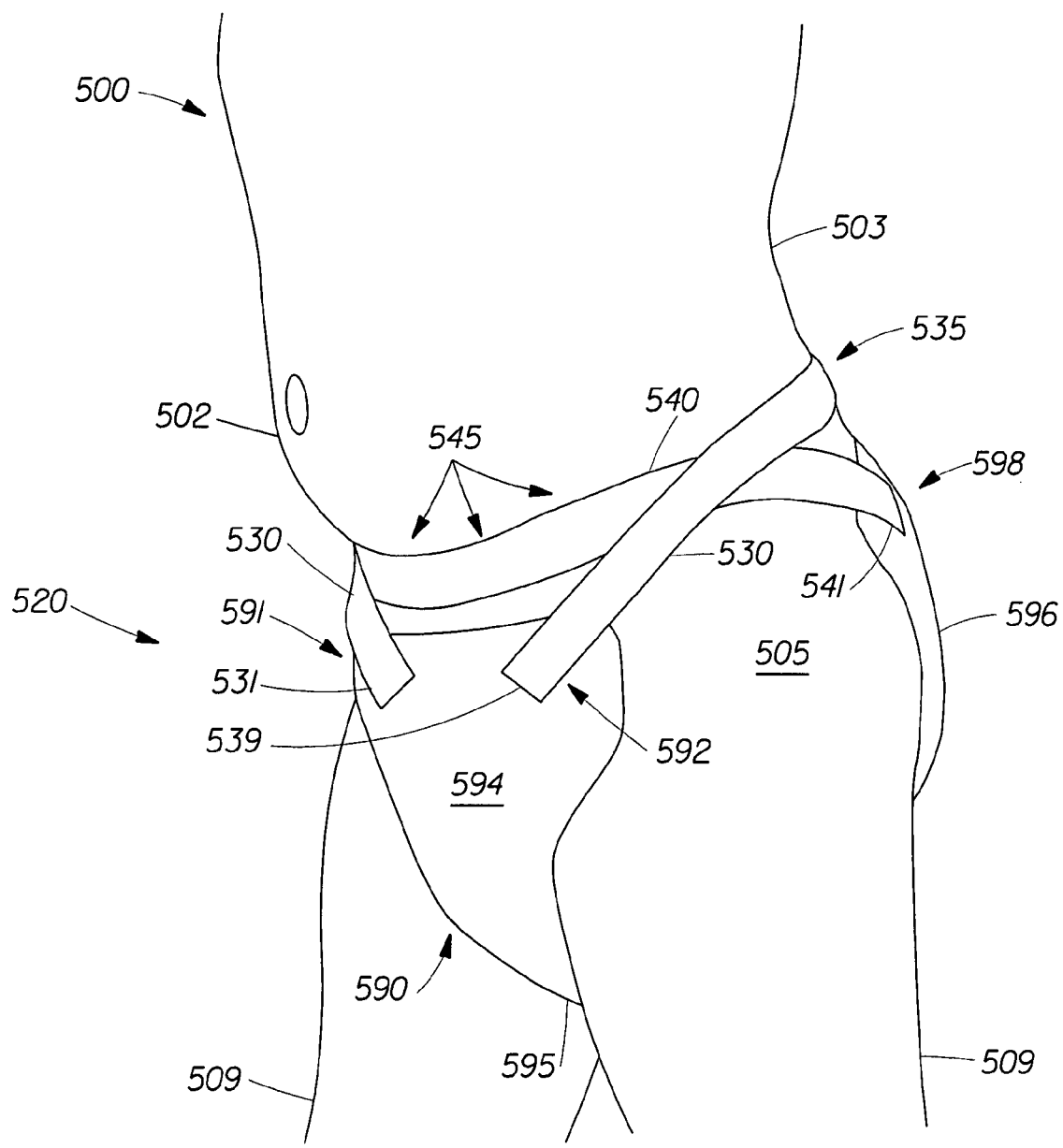
FIG. 5 illustrates a perspective view of an embodiment of an anchoring system and an absorbent core for use in a disposable wearable absorbent article, as worn on a wearer, according to the present disclosure.

FIG. 5 illustrates a perspective view of an embodiment of an anchoring system 520 and an absorbent core 590 for use in a disposable wearable absorbent article, as worn on a wearer 500, according to the present disclosure. The wearer 500 includes a belly 502, a back 503, a hip 505, and upper legs 509. The anchoring system 520 is joined to the absorbent core 590. The anchoring system 520 is configured for use in a disposable wearable absorbent article with a front and back, as described herein. The absorbent core 590 includes a front portion 594 disposed in the front, a crotch region 595, and a back portion 596 disposed in the back. The anchoring system 520 includes a first CAM 530 with a first end 531 joined to the front portion 594, a first middle 535 disposed across the back, and a second end 539 joined to the front portion 594. The first end 531 is directly connected to the front portion 594 at a first location 591 and the second end 539 is directly connected to the front portion 594 at a second location 592 that is laterally spaced apart from the first location 591.

The anchoring system 520 also includes a second CAM 540 with a third end 541 joined to the back portion 596, a second middle 545 disposed across the front, and a fourth end joined to the back portion 596. The third end 541 is directly connected to the back portion 596 at a third location 598. The fourth end is directly connected to the back portion 596 at a fourth location that is laterally spaced apart from the third location 598. In various embodiments, the anchoring system 520 can alternatively include a second CAM configured with the back portion 596 as described in connection with the second CAM 340 of the embodiment of FIGS. 3A and 3B, the second CAM 440 of the embodiment of FIG. 4, or the second CAM 640 of the embodiment of FIG. 6, as will be understood by one of ordinary skill in the art.

Figure 6:
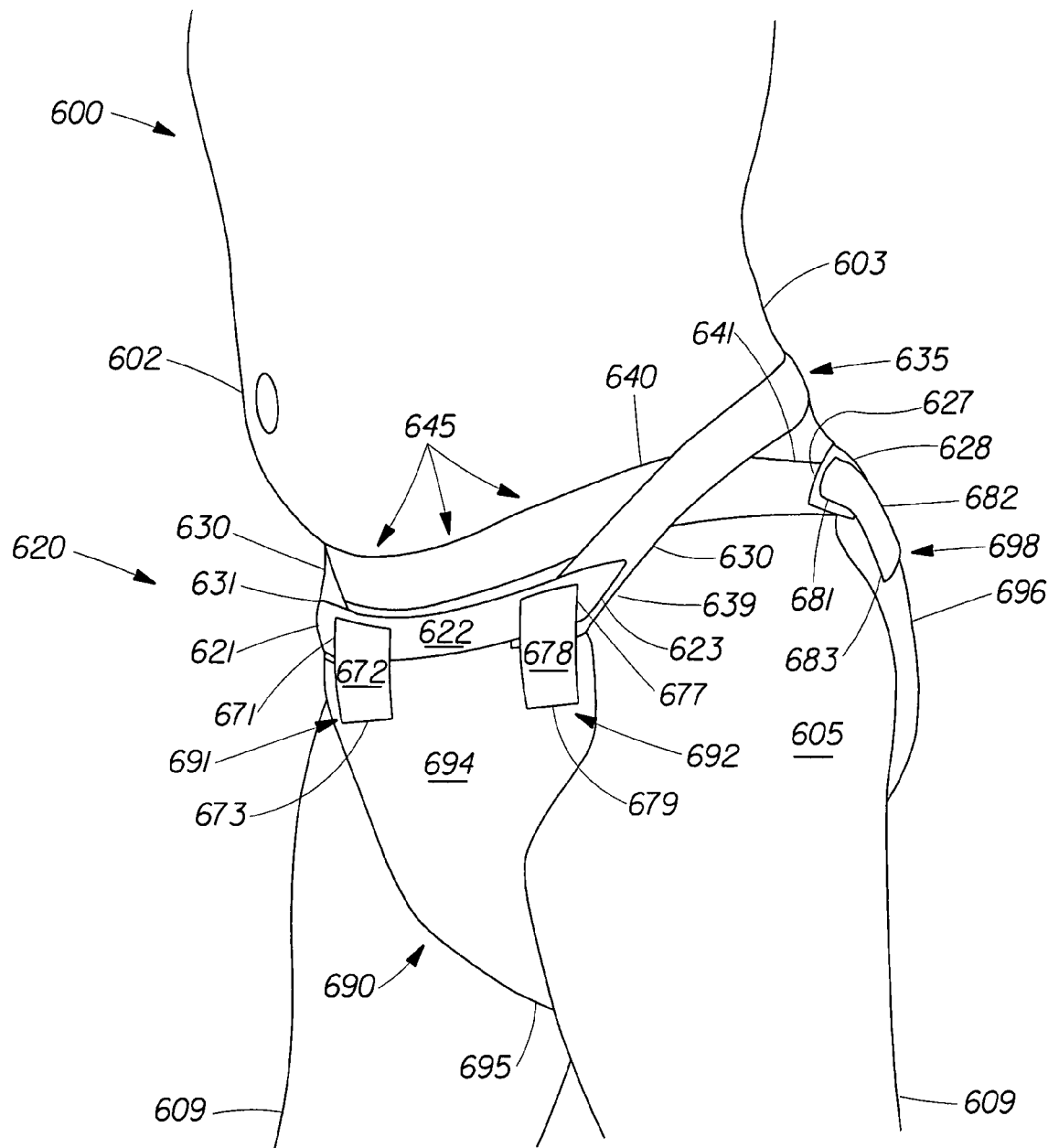
FIG. 6 illustrates a perspective view of an embodiment of an anchoring system and an absorbent core for use in a disposable wearable absorbent article, as worn on a wearer, according to the present disclosure.

FIG. 6 illustrates a perspective view of an embodiment of an anchoring system 620 and an absorbent core 690 for use in a disposable wearable absorbent article, as worn on a wearer 600, according to the present disclosure. The wearer 600 includes a belly 602, a back 603, a hip 605, and upper legs 609. The anchoring system 620 is joined to the absorbent core 690. The anchoring system 620 is configured for use in a disposable wearable absorbent article with a front and back, as described herein. The absorbent core 690 includes a front portion 694 disposed in the front, a crotch region 695, and a back portion 696 disposed in the back. The anchoring system 620 includes a first CAM 630 with a first end 631 joined to the front portion 694, a first middle 635 disposed across the back, and a second end 639 joined to the front portion 694.

The anchoring system 620 includes a front anchoring band 622 with front anchoring band ends 621 and 623. The anchoring system 620 also includes a first LDE 672 with first LDE ends 671 and 673 and a second LDE 678 with second LDE ends 677 and 679. The first end 631 is joined to the front anchoring band 622 at the front anchoring band end 621 and also joined to the first LDE 672 at the first LDE end 671. The second end 639 is joined to the front anchoring band 622 at the front anchoring band end 623 and also joined to the second LDE 678 at the second LDE end 677. The first LDE end 673 of the first LDE 672 is directly connected to the front portion 694 at a first LDE location 691 and the second LDE end 679 of the second LDE 678 is directly connected to the front portion 694 at a second LDE location 692 that is laterally spaced apart from the first LDE location 691.

The anchoring system 620 includes a second CAM 640 with a third end 641 joined to the back portion 696, a second middle 645 disposed across the front, and a fourth end joined to the back portion 696. The anchoring system 620 includes a back anchoring band 628 with a back anchoring band end 627. The anchoring system 620 further includes a third LDE 682 with third LDE ends 681 and 683 and a fourth LDE with fourth LDE ends. The third end 641 is joined to the back anchoring band 628 at the back anchoring band end 627 and also joined to the fourth LDE 682 at the fourth LDE end 681. The fourth end is joined to the back anchoring band 628 and also joined to the fourth LDE at a fourth LDE end. The third LDE end 683 of the third LDE 682 is directly connected to the back portion 696 at a third LDE location 698 and a fourth LDE end of the fourth LDE is directly connected to the back portion 696 at a fourth LDE location that is laterally spaced apart from the third LDE location. In various embodiments of the anchoring system 620, more or fewer LDEs can be used. In various embodiments, the anchoring system 620 can alternatively include a second CAM configured with the back portion 696 as described in connection with the second CAM 340 of the embodiment of FIGS. 3A and 3B, the second CAM 440 of the embodiment of FIG. 4, or the second CAM 540 of the embodiment of FIG. 5, as will be understood by one of ordinary skill in the art.

Figure 7A:
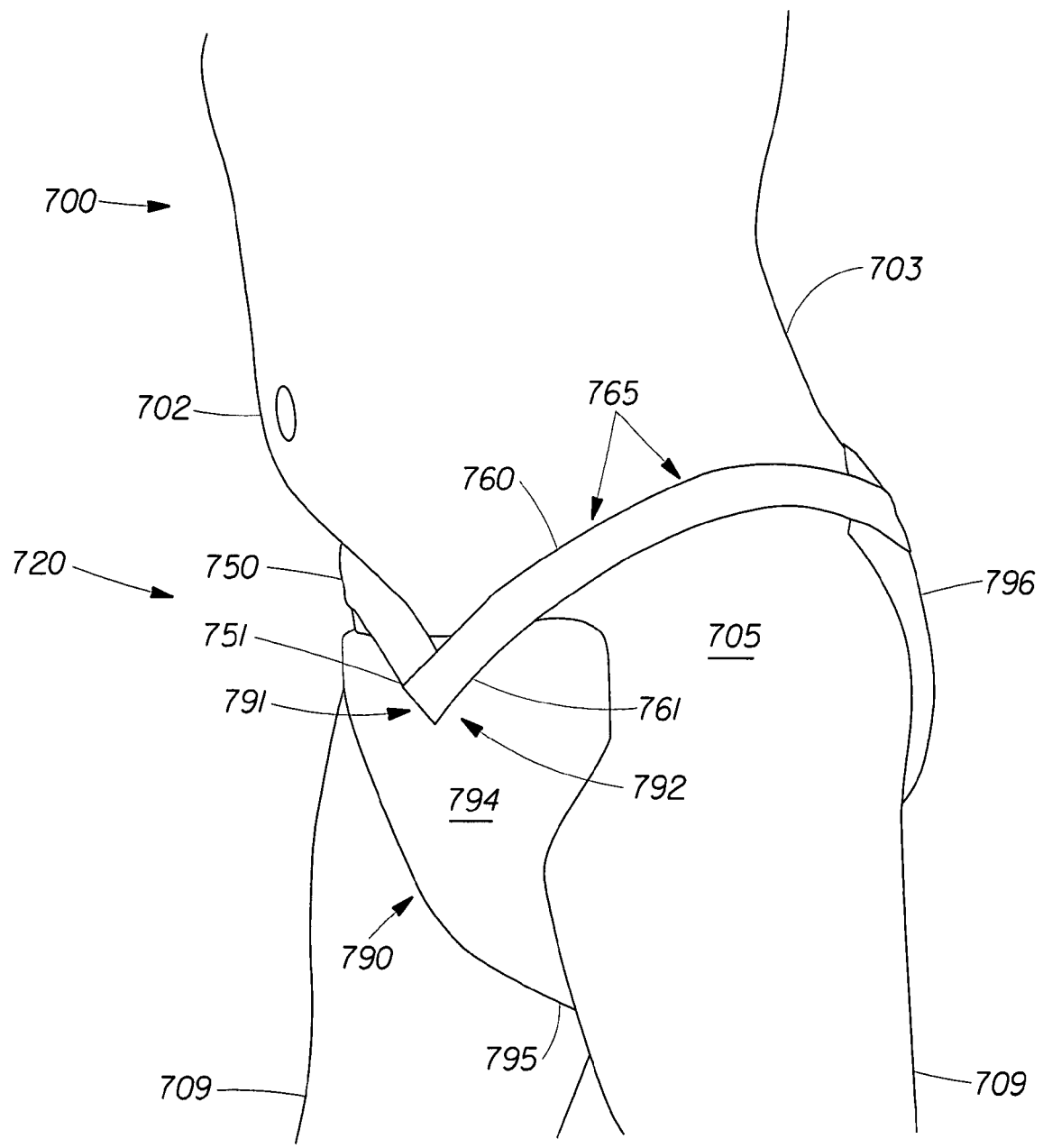
FIG. 7A illustrates a perspective view of an embodiment of an anchoring system and an absorbent core for use in a disposable wearable absorbent article, as worn on a wearer, according to the present disclosure.

FIG. 7A illustrates a perspective view of an embodiment of an anchoring system 720 and an absorbent core 790 for use in a disposable wearable absorbent article, as worn on a wearer 700, according to the present disclosure. The wearer 700 includes a belly 702, a back 703, a hip 705, and upper legs 709. The anchoring system 720 is joined to the absorbent core 790. The anchoring system 720 is configured for use in a disposable wearable absorbent article with a front and back, as described herein. The absorbent core 790 includes a front portion 794 disposed in the front, a crotch region 795, and a back portion 796 disposed in the back. The anchoring system 720 includes a first CAM 750 with a first end 751 joined to the front portion 794, a first middle disposed across a second side, and a fourth end joined to the back portion 796. The anchoring system 720 also includes a second CAM 760 with a second end 761 joined to the front portion 794, a second middle 765 disposed across a first side, and a third end joined to the back portion 796.

The first end 751 is directly connected to the front portion 794 at a first location 791. The second end 761 is directly connected to the front portion 794 at a second location 792 that at least partially overlaps the first location 791. The third end is directly connected to the back portion 796 at a third location. The fourth end is directly connected to the back portion 796 at a fourth location that at least partially overlaps the third location. In various embodiments, the anchoring system 720 can alternatively include a first CAM and a second CAM configured with the back portion 796 as described in connection with a first CAM 850 and a second CAM 860 of the embodiment of FIG. 8, a first CAM 950 and a second CAM 960 of the embodiment of FIG. 9, or a first CAM 1050 and a second CAM 1060 of the embodiment of FIG. 10 as will be understood by one of ordinary skill in the art.

Figure 7B:
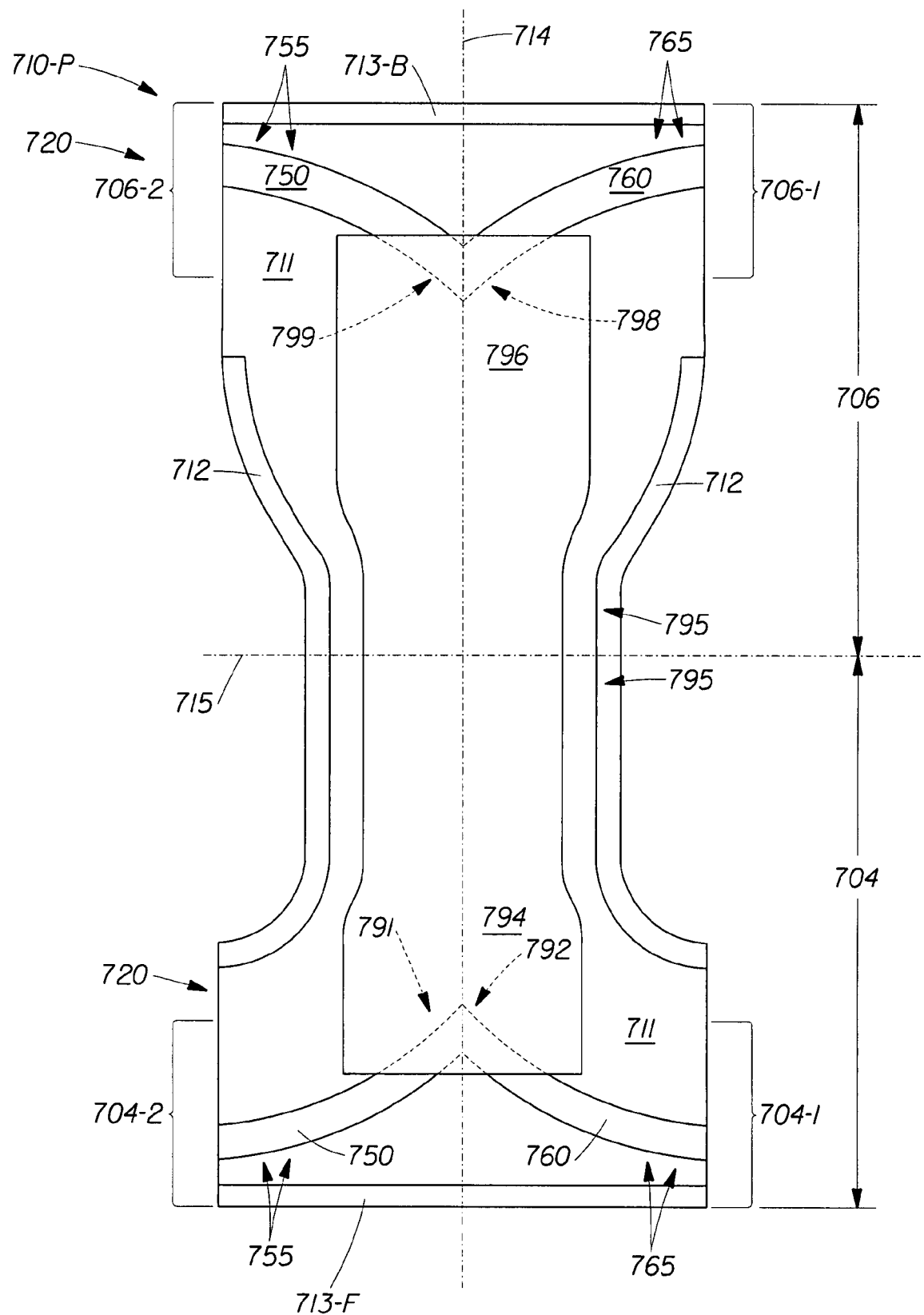
FIG. 7B illustrates a plan view of an embodiment of a pant-type disposable wearable absorbent article including the anchoring system of the embodiment of FIG. 7A, according to the present disclosure.

FIG. 7B illustrates a plan view of an embodiment of a pant-type disposable wearable absorbent article 710-P including the anchoring system 720 of the embodiment of FIG. 7A, according to the present disclosure. The pant-type disposable wearable absorbent article 710-P includes a front 704 with a first front side interface 704-1 and a second front side interface 704-2 and a back 706 with a first back side interface 706-1 and a second back side interface 706-2. The first front side interface 704-1 and the first back side interface 706-1 can be joined to form a first side interface between the front 704 and the back 706. The second front side interface 704-2 and the second back side interface 706-2 can also be joined to form a second side interface between the front 704 and the back 706. Thus, the first and second side interfaces can each carry tension for the first CAM 750 and/or the second CAM 760 between the front 704 and the back 706.

The pant-type disposable wearable absorbent article 710-P also includes a chassis 711, leg bands 712, a waistband with a front portion of the waistband 713-F and a back portion of the waistband 713-B, a longitudinal centerline 714, and a lateral centerline 715. The lateral centerline 715 forms a boundary between the front 704 and the back 706 in the pant-type disposable wearable absorbent article 710-P. The pant-type disposable wearable absorbent article 710-P includes the absorbent core 790 with the front portion 794 disposed in the front 704, the crotch region 795 disposed generally around the lateral centerline 715, and the back portion 796 disposed in the back 706. The anchoring system 720 is joined to the absorbent core 790.

The anchoring system 720 includes the first CAM 750 with the first end joined to the front portion 794, the first middle 755 disposed through the second side interface, and the fourth end joined to the back portion 796. The first end is directly connected to the front portion 794 at the first location 791 and the fourth end is directly connected to the back portion 796 at the fourth location 799. The anchoring system 720 also includes the second CAM 760 with the second end joined to the front portion 794, the second middle 765 disposed through the first side interface, and the third end joined to the back portion 796. The second end is directly connected to the front portion 794 at the second location 792 and the third end is directly connected to the back portion 796 at the third location 799. The first location 791 at least partially overlaps the second location 792 and the third location 798 at least partially overlaps the fourth location 799.

In some embodiments, the first CAM 750) and the second CAM 760 of the anchoring system 720 can each be configured as open geodesics. The first CAM 750 can be considered an open geodesic as has two endpoints and does not intersect itself it wraps around a portion of a body of the wearer 700. The second CAM 740 can also be considered an open geodesic as it also has two endpoints and does not intersect itself it wraps around a portion of a body of the wearer 700. As a result, the anchoring system 720 can be configured to geodesically anchor the absorbent core 790 to the wearer 700. Similarly, CAMs in the anchoring system embodiments of FIGS. 8-12 can also be configured as open geodesics, as will be understood by one of ordinary skill in the art.

Figure 8:
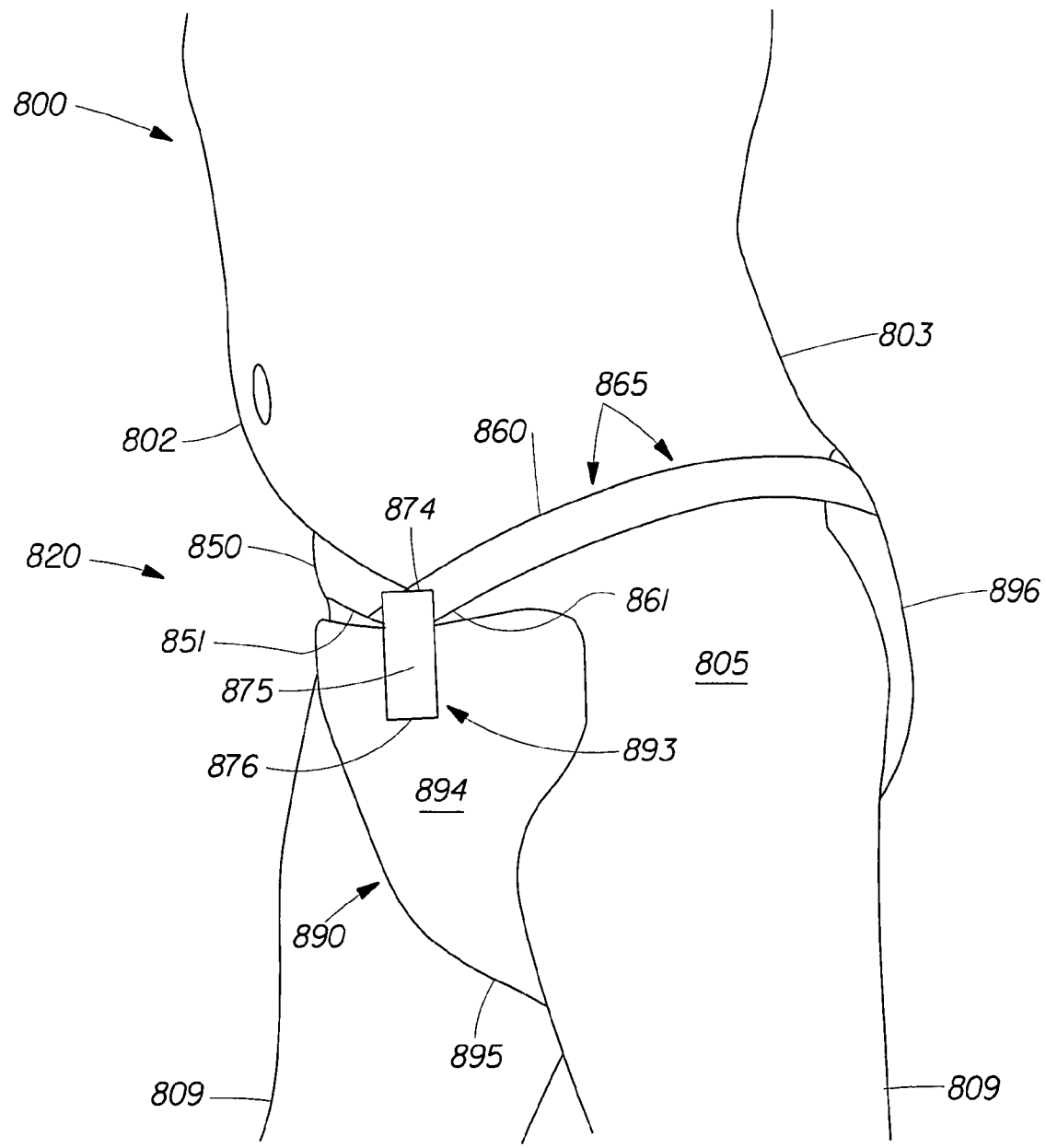
FIG. 8 illustrates a perspective view of an embodiment of an anchoring system and an absorbent core for use in a disposable wearable absorbent article, as worn on a wearer, according to the present disclosure.

FIG. 8 illustrates a perspective view of an embodiment of an anchoring system 820 and an absorbent core 890 for use in a disposable wearable absorbent article, as worn on a wearer 800, according to the present disclosure. The wearer 800 includes a belly 802, a back 803, a hip 805, and upper legs 809. The anchoring system 820 is joined to the absorbent core 890. The anchoring system 820 is configured for use in a disposable wearable absorbent article with a front and back, as described herein. The absorbent core 890 includes a front portion 894 disposed in the front, a crotch region 895, and a back portion 896 disposed in the back. The anchoring system 820 includes a first CAM 850 with a first end 851 joined to the front portion 894, a first middle disposed across a second side, and a fourth end joined to the back portion 896. The anchoring system 820 also includes a second CAM 860 with a second end 861 joined to the front portion 894, a second middle 865 disposed across a first side, and a third end joined to the back portion 896.

The anchoring system 820 includes a front LDE 875 with front LDE ends 874 and 876. The first end 851 and the second end 861 are each joined to the front LDE 875 at the front LDE end 874. The front LDE end 876 of the front LDE 875 is directly connected to the front portion 894 at a front LDE location 893. The anchoring system 820 also includes a back LDE. The third end and the fourth end are each joined to the back LDE and the back LDE is directly connected to the back portion 896. In various embodiments of the anchoring system 820, more or fewer LDEs can be used. In various embodiments, the anchoring system 820 can alternatively include a first CAM and a second CAM configured with the back portion 896 as described in connection with the first CAM 750 and the second CAM 760 of the embodiment of FIGS. 7A and 7B, the first CAM 950 and the second CAM 960 of the embodiment of FIG. 9, or the first CAM 1050 and the second CAM 1060 of the embodiment of FIG. 10 as will be understood by one of ordinary skill in the art.

Figure 9:
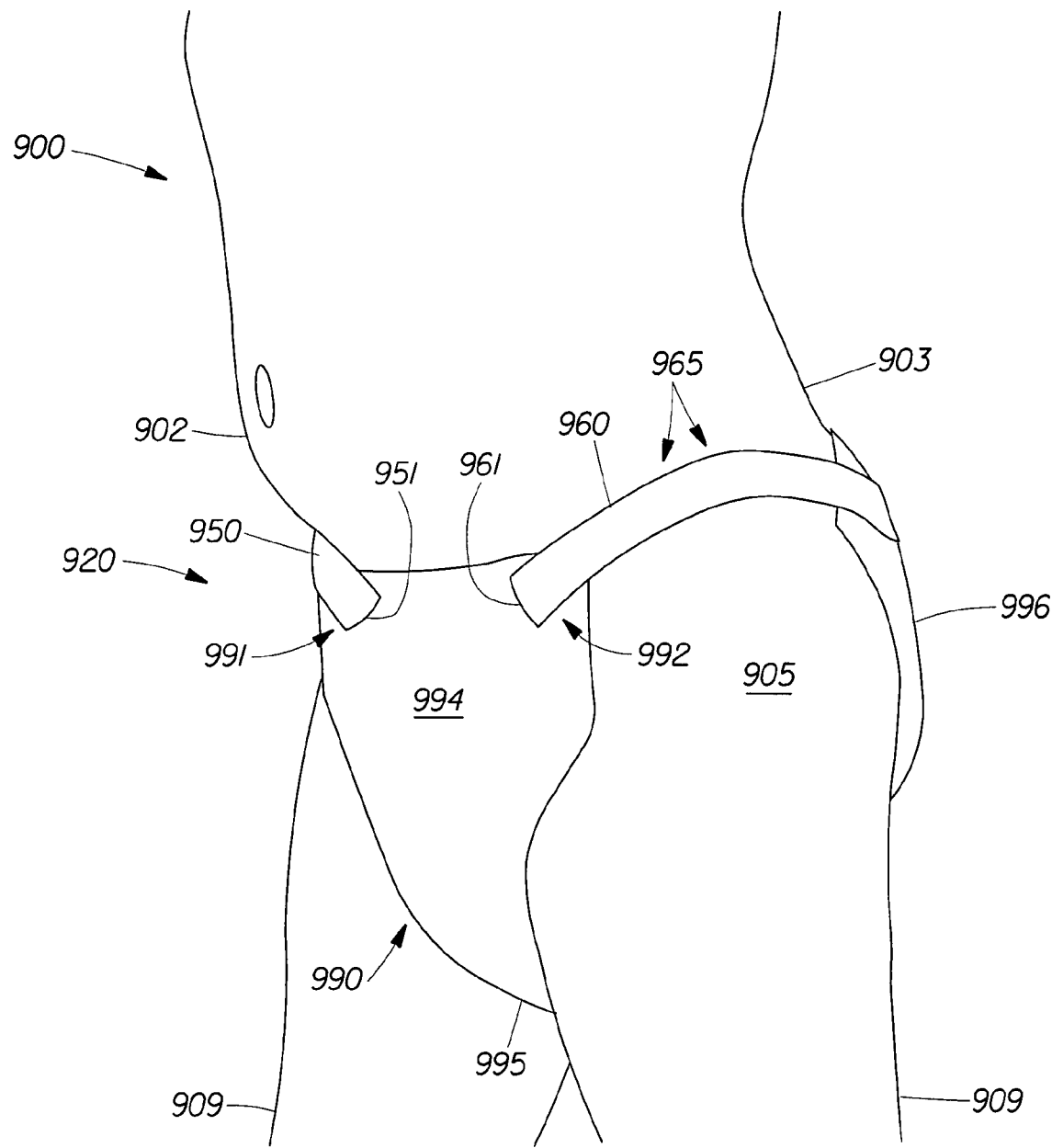
FIG. 9 illustrates a perspective view of an embodiment of an anchoring system and an absorbent core for use in a disposable wearable absorbent article, as worn on a wearer, according to the present disclosure.

FIG. 9 illustrates a perspective view of an embodiment of an anchoring system 920 and an absorbent core 990 for use in a disposable wearable absorbent article, as worn on a wearer 900, according to the present disclosure. The wearer 900 includes a belly 902, a back 903, a hip 905, and upper legs 909. The anchoring system 920 is joined to the absorbent core 990. The anchoring system 920 is configured for use in a disposable wearable absorbent article with a front and back, as described herein. The absorbent core 990 includes a front portion 994 disposed in the front, a crotch region 995, and a back portion 996 disposed in the back. The anchoring system 920 includes a first CAM 950 with a first end 951 joined to the front portion 994, a first middle disposed across a second side, and a fourth end joined to the back portion 996. The anchoring system 920 also includes a second CAM 960 with a second end 961 joined to the front portion 994, a second middle 965 disposed across a first side, and a third end joined to the back portion 996.

The first end 951 is directly connected to the front portion 994 at a first location 991. The second end 961 is directly connected to the front portion 994 at a second location 992 that is laterally spaced apart from the first location 991. The third end is directly connected to the back portion 996 at a third location. The fourth end is directly connected to the back portion 996 at a fourth location that is laterally spaced apart from the third location. In various embodiments, the anchoring system 920 can alternatively include a first CAM and a second CAM configured with the back portion 996 as described in connection with the first CAM 750 and the second CAM 760 of the embodiment of FIGS. 7A and 7B, the first CAM 850 and the second CAM 860 of the embodiment of FIG. 8, or the first CAM 1050 and the second CAM 1060 of the embodiment of FIG. 10 as will be understood by one of ordinary skill in the art.

Figure 10:
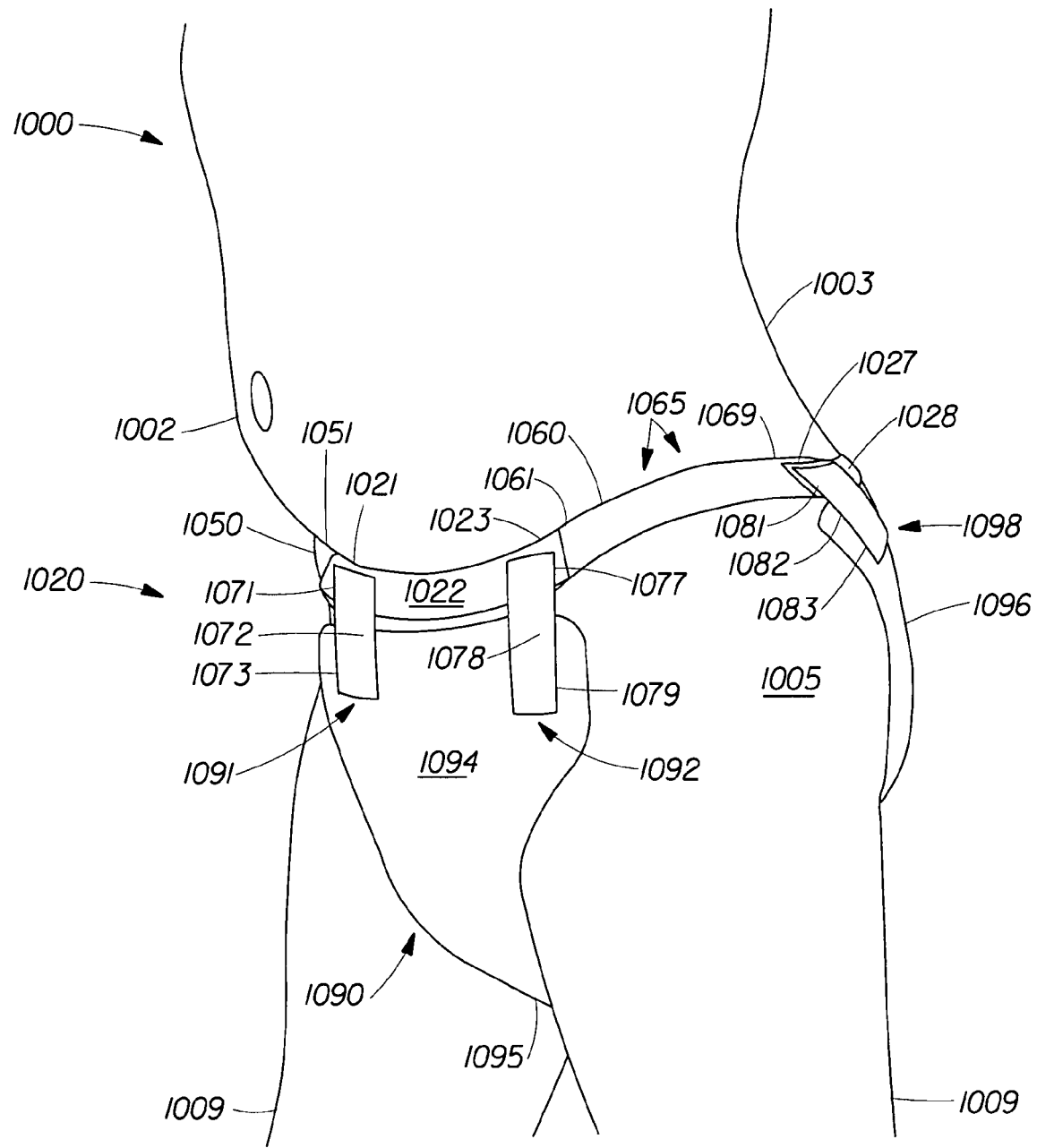
FIG. 10 illustrates a perspective view of an embodiment of an anchoring system and an absorbent core for use in a disposable wearable absorbent article, as worn on a wearer, according to the present disclosure.

FIG. 10 illustrates a perspective view of an embodiment of an anchoring system 1020 and an absorbent core 1090 for use in a disposable wearable absorbent article, as worn on a wearer 1000, according to the present disclosure. The wearer 1000 includes a belly 1002, a back 1003, a hip 1005, and upper legs 1009. The anchoring system 1020 is joined to the absorbent core 1090. The anchoring system 1020 is configured for use in a disposable wearable absorbent article with a front and back, as described herein. The absorbent core 1090 includes a front portion 1094 disposed in the front, a crotch region 1095, and a back portion 1096 disposed in the back. The anchoring system 1020 includes a first CAM 1050 with a first end 1051 joined to the front portion 1094, a first middle disposed across a second side, and a fourth end joined to the back portion 1096. The anchoring system 1020 also includes a second CAM 1060 with a second end 1061 joined to the front portion 1094, a second middle 1065 disposed across a first side, and a third end 1069 joined to the back portion 1096.

The anchoring system 1020 includes a front anchoring band 1022 with front anchoring band ends 1021 and 1023. The anchoring system 1020 also includes a first LDE 1072 with first LDE ends 1071 and 1073 and a second LDE 1078 with second LDE ends 1077 and 1079. The first end 1051 is joined to the front anchoring band 1022 at the front anchoring band end 1021 and also joined to the first LDE 1072 at the first LDE end 1071. The second end 1061 is joined to the front anchoring band 1022 at the front anchoring band end 1023 and also joined to the second LDE 1078 at the second LDE end 1077. The first LDE end 1073 of the first LDE 1072 is directly connected to the front portion 1094 at a first LDE location 1091 and the second LDE end 1079 of the second LDE 1078 is directly connected to the front portion 1094 at a second LDE location 1092 that is laterally spaced apart from the first LDE location 1091.

The anchoring system 1020 includes a back anchoring band 1028 with a back anchoring band end 1027. The anchoring system 1020 further includes a third LDE 1082 with third LDE ends 1081 and 1083 and a fourth LDE with fourth LDE ends. The third end 1069 is joined to the back anchoring band 1028 at the back anchoring band end 1027 and also joined to the third LDE 1082 at the third LDE end 1081. The fourth end is joined to the back anchoring band 1028 and also joined to the fourth LDE at a fourth LDE end. The third LDE end 1083 of the third LDE 1082 is directly connected to the back portion 1096 at a third LDE location 1098 and a fourth LDE end of the fourth LDE is directly connected to the back portion 1096 at a fourth LDE location and that is laterally spaced apart from the third LDE location 1098. In various embodiments of the anchoring system 1020, more or fewer LDEs can be used. In various embodiments, the anchoring system 1020 can alternatively include a first CAM and a second CAM configured with the back portion 1096 as described in connection with the first CAM 750 and the second CAM 760 of the embodiment of FIGS. 7A and 7B, the first CAM 850 and the second CAM 860 of the embodiment of FIG. 8, or the first CAM 950 and the second CAM 960 of the embodiment of FIG. 9 as will be understood by one of ordinary skill in the art.

Figure 11A:
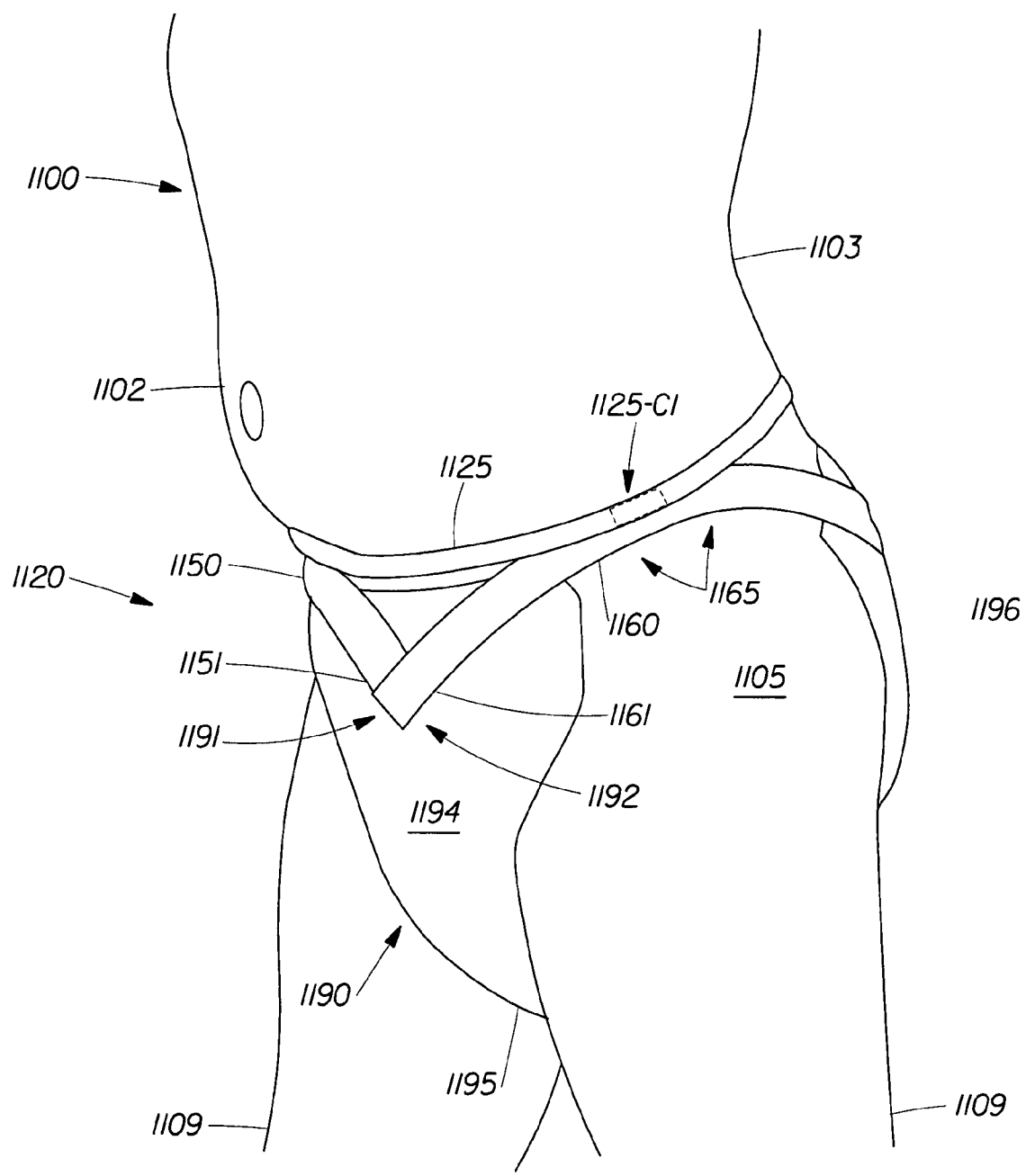
FIG. 11A illustrates a perspective view of an embodiment of an anchoring system and an absorbent core for use in a disposable wearable absorbent article, as worn on a wearer, according to the present disclosure.

FIG. 11A illustrates a perspective view of an embodiment of an anchoring system 1120 and an absorbent core 1190 for use in a disposable wearable absorbent article, as worn on a wearer 1100, according to the present disclosure. The wearer 1100 includes a belly 1102, a back 1103, a hip 1105, and upper legs 1109. The anchoring system 1120 is joined to the absorbent core 1190. The anchoring system 1120 is configured for use in a disposable wearable absorbent article with a front and back, as described herein. The absorbent core 1190 includes a front portion 1194 disposed in the front, a crotch region 1195, and a back portion 1196 disposed in the back. The anchoring system 1120 includes a first CAM 1150 with a first end 1151 joined to the front portion 1194, a first middle disposed across a second side, and a fourth end joined to the back portion 1196. The anchoring system 1120 also includes a second CAM 1160 with a second end 1161 joined to the front portion 1194, a second middle 1165 disposed across a first side, and a third end joined to the back portion 1196. The first end 1151 is directly connected to the front portion 1194 at a first location 1191. The second end 1161 is directly connected to the front portion 1194 at a second location 1192 that at least partially overlaps the first location 1191. The anchoring system 1120 also includes a continuous stabilizing band 1125 disposed continuously across the front and the back. The first middle is directly connected to the continuous stabilizing band 1125 on the second side and the second middle 1165 is directly connected to the continuous stabilizing band 1125 on the first side at a first stabilizing band connection location 1125-C1.

Figure 11B:
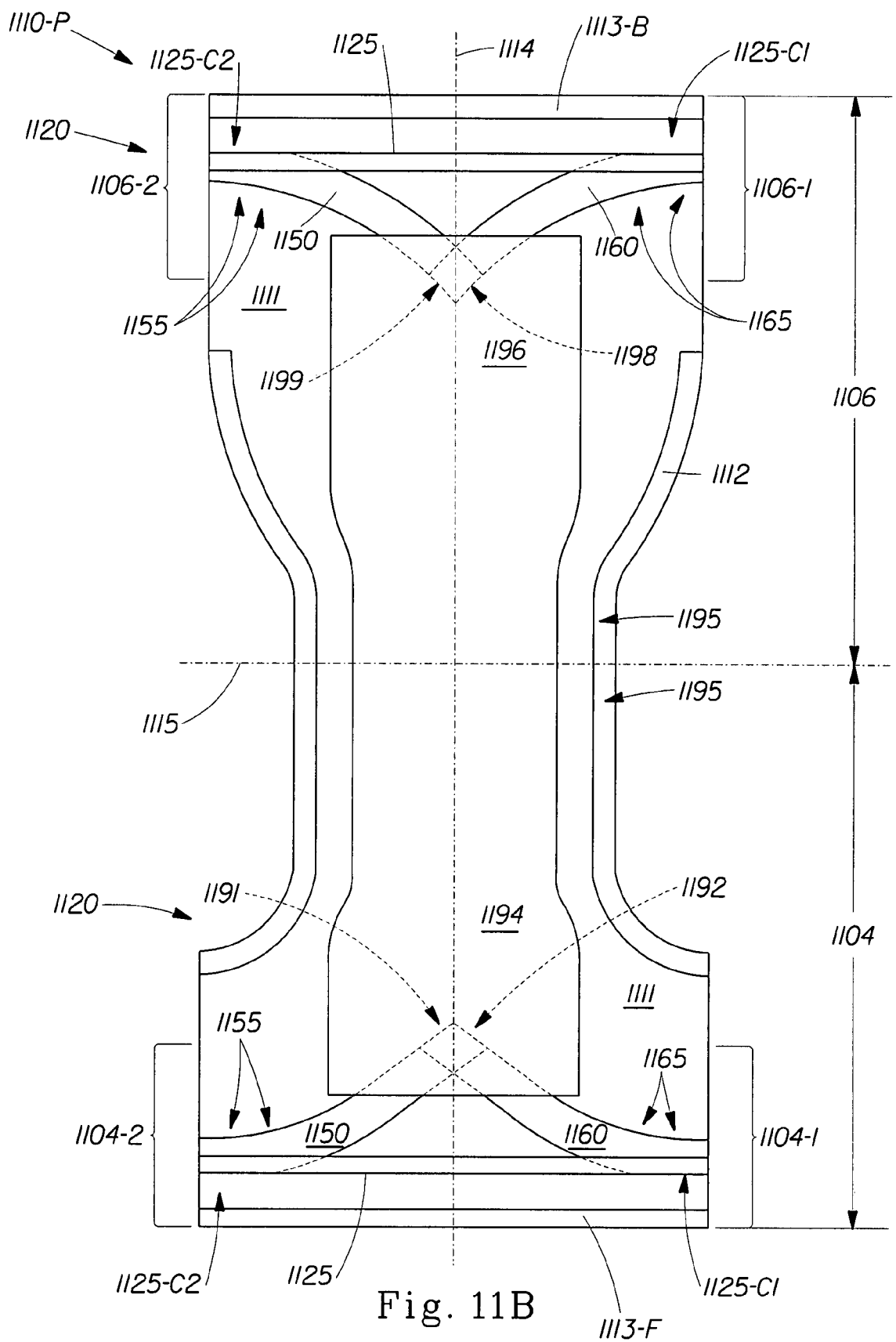
FIG. 11B illustrates a plan view of an embodiment of a pant-type disposable wearable absorbent article including the anchoring system of the embodiment of FIG. 11A, according to the present disclosure.

FIG. 11B illustrates a plan view of an embodiment of a pant-type disposable wearable absorbent article 1110-P including the anchoring system 1120 of the embodiment of FIG. 11A, according to the present disclosure. The pant-type disposable wearable absorbent article 1110-P includes a front 1104 with a first front side interface 1104-1 and a second front side interface 1104-2 and a back 1106 with a first back side interface 1106-1 and a second back side interface 1106-2. The first front side interface 1104-1 and the first back side interface 1106-1 can be joined to form a first side interface between the front 1104 and the back 1106. The second front side interface 1104-2 and the second back side interface 1106-2 can also be joined to form a second side interface between the front 1104 and the back 1106. Thus, the first and second side interfaces can each carry tension for the first CAM 1150 and/or the second CAM 1160 between the front 1104 and the back 1106.

The pant-type disposable wearable absorbent article 1110-P also includes a chassis 1111, leg bands 1112, a waistband with a front portion of the waistband 1113-F and a back portion of the waistband 1113-B, a longitudinal centerline 1114, and a lateral centerline 1115. The lateral centerline 1115 forms a boundary between the front 1104 and the back 1106 in the pant-type disposable wearable absorbent article 1110-P. The pant-type disposable wearable absorbent article 1110-P includes the absorbent core 1190 with the front portion 1194 disposed in the front 1104, the crotch region 1195 disposed generally around the lateral centerline 1115, and the back portion 1196 disposed in the back 1106. The anchoring system 1120 is joined to the absorbent core 1190.

The anchoring system 1120 includes the first CAM 1150 with the first end joined to the front portion 1194, the first middle 1155 disposed through the second side interface, and the fourth end joined to the back portion 1196. The first end is directly connected to the front portion 1194 at the first location 1191 and the fourth end is directly connected to the back portion 1196 at the fourth location 1199. The anchoring system 1120 also includes the second CAM 1160 with the second end joined to the front portion 1194, the second middle 1165 disposed through the first side interface, and the third end joined to the back portion 1196. The second end is directly connected to the front portion 1194 at the second location 1192 and the third end is directly connected to the back portion 1196 at the third location 1199. The first location 1191 at least partially overlaps the second location 1192 and the third location 1198 at least partially overlaps the fourth location 1199. The anchoring system 1120 also includes the continuous stabilizing band 1125 disposed continuously across the front 1104 and the back 1106. The first middle 1155 is directly connected to the continuous stabilizing band 1125 on the second side at a second stabilizing band connection location 1125-C1. The second middle 1165 is directly connected to the continuous stabilizing band 1125 on the first side at the first stabilizing band connection location 1125-C1.

Figure 12:
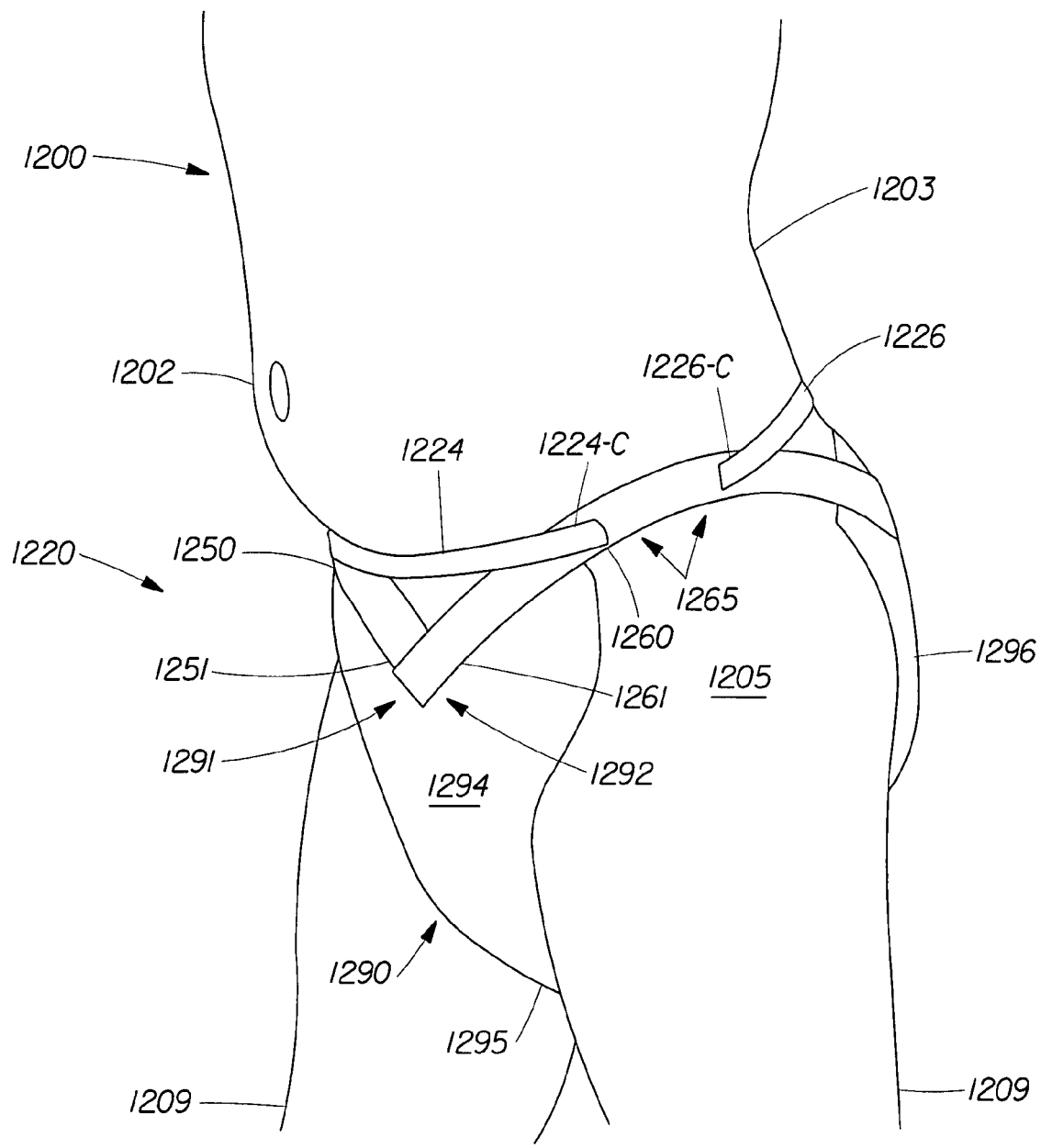
FIG. 12 illustrates a perspective view of an embodiment of an anchoring system and an absorbent core for use in a disposable wearable absorbent article, as worn on a wearer, according to the present disclosure.

FIG. 12 illustrates a perspective view of an embodiment of an anchoring system 1220 and an absorbent core 1290 for use in a disposable wearable absorbent article, as worn on a wearer 1200, according to the present disclosure. The wearer 1200 includes a belly 1202, a back 1203, a hip 1205, and upper legs 1209. The anchoring system 1220 is joined to the absorbent core 1290. The anchoring system 1220 is configured for use in a disposable wearable absorbent article with a front and back, as described herein. The absorbent core 1290 includes a front portion 1294 disposed in the front, a crotch region 1295, and a back portion 1296 disposed in the back. The anchoring system 1220 includes a first CAM 1250 with a first end 1251 joined to the front portion 1294, a first middle disposed across a second side, and a fourth end joined to the back portion 1296. The anchoring system 1220 also includes a second CAM 1260 with a second end 1261 joined to the front portion 1294, a second middle 1265 disposed across a first side, and a third end joined to the back portion 1296. The first end 1251 is directly connected to the front portion 1294 at a first location 1291. The second end 1261 is directly connected to the front portion 1294 at a second location 1292 that at least partially overlaps the first location 1291. The anchoring system 1220 also includes a front stabilizing band 1224 and a back stabilizing band 1226. The front stabilizing band 1224 is directly connected to the first CAM 1250, directly connected to the second CAM at a front stabilizing band connection location 1224-C, and disposed at least in part in the front. The back stabilizing band 1226 is directly connected to the first CAM 1250, directly connected to the second CAM at a back stabilizing band connection location 1226-C, and disposed at least in part in the back.

Figure 13:
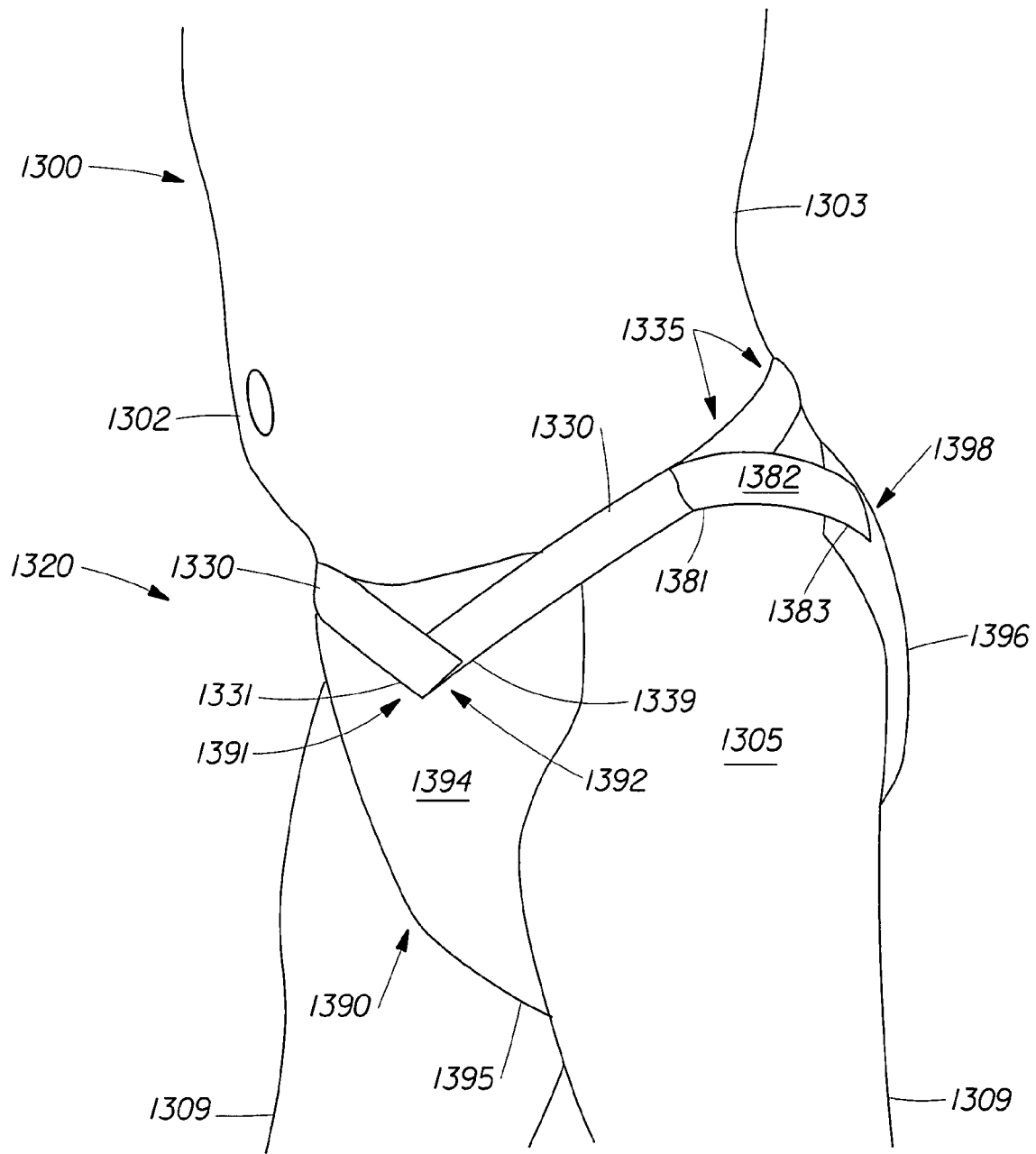
FIG. 13 illustrates a perspective view of an embodiment of an anchoring system and an absorbent core for use in a disposable wearable absorbent article, as worn on a wearer, according to the present disclosure.

FIG. 13 illustrates a perspective view of an embodiment of an anchoring system 1320 and an absorbent core 1390 for use in a disposable wearable absorbent article, as worn on a wearer 1300, according to the present disclosure. The wearer 1300 includes a belly 1302, a back 1303, a hip 1305, and upper legs 1309. The anchoring system 1320 is joined to the absorbent core 1390. The anchoring system 1320 is configured for use in a disposable wearable absorbent article with a front and back, as described herein. The absorbent core 1390 includes a front portion 1394 disposed in the front, a crotch region 1395, and a back portion 1396 disposed in the back. The anchoring system 1320 includes a first CAM 1330 with a first end 1331 joined to the front portion 1394, a first middle 1335 disposed across the back, and a second end 1339 joined to the front portion 1394. The first end 1331 is directly connected to the front portion 1394 at a first location 1391 and the second end 1339 is directly connected to the front portion 1394 at a second location 1392 that at least partially overlaps the first location 1391. The anchoring system 1320 includes a third LDE 1382 with third LDE ends 1381 and 1383 and a fourth LDE with fourth LDE ends. The third LDE end 1381 of the third LDE 1382 is directly connected to the first middle 1335 and the third LDE end 1383 is directly connected to the back portion 1396 at the a third LDE location 1398. A fourth LDE end of the fourth LDE is directly connected to the first middle 1335 and a fourth LDE end of the fourth LDE is directly connected to the back portion 1396 at a fourth LDE location. In various embodiments of the anchoring system 1320, more or fewer LDEs can be used.

Figure 14:
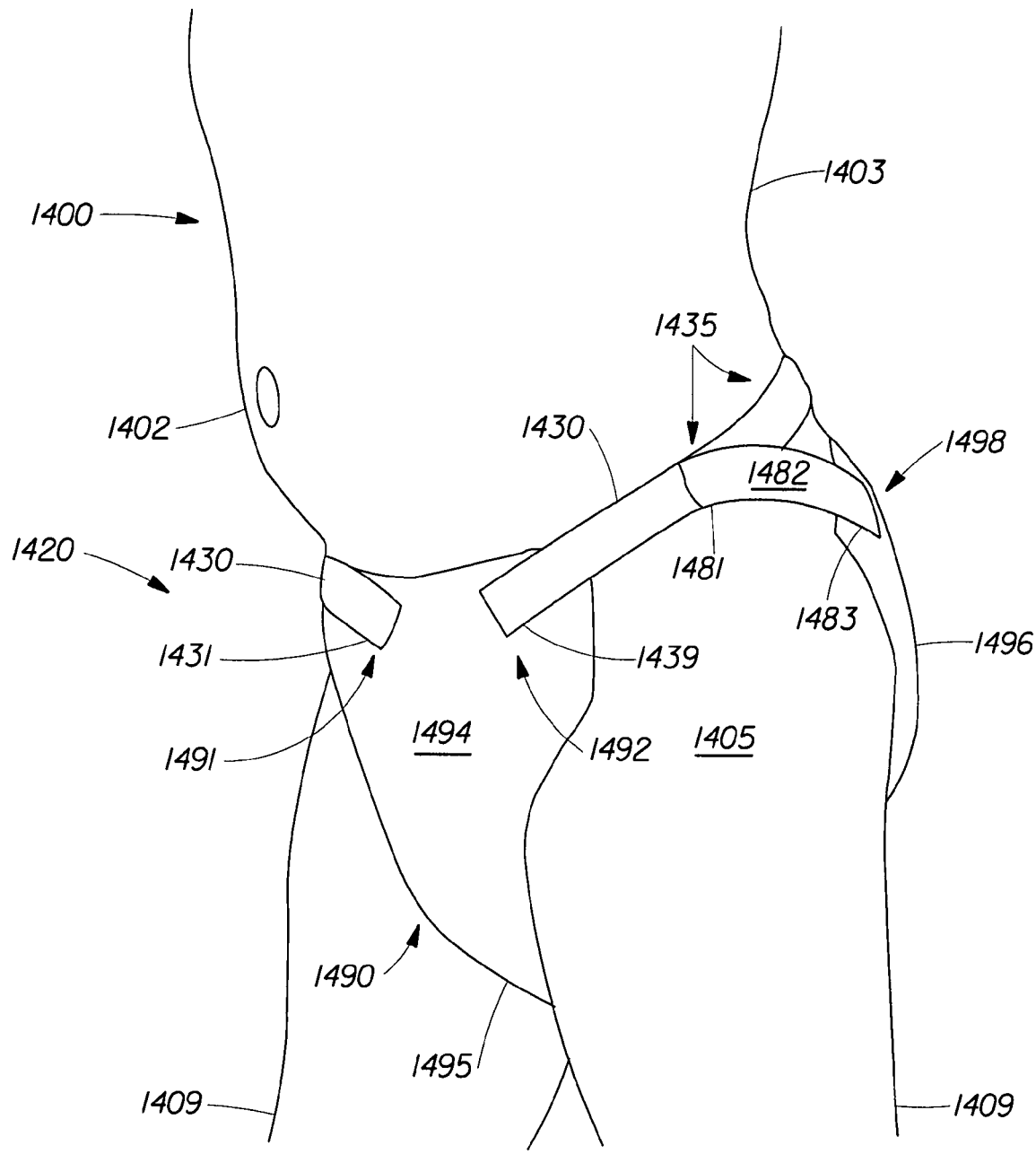
FIG. 14 illustrates a perspective view of an embodiment of an anchoring system and an absorbent core for use in a disposable wearable absorbent article, as worn on a wearer, according to the present disclosure.

FIG. 14 illustrates a perspective view of an embodiment of an anchoring system 1420 and an absorbent core 1490 for use in a disposable wearable absorbent article, as worn on a wearer 1400, according to the present disclosure. The wearer 1400 includes a belly 1402, a back 1403, a hip 1405, and upper legs 1409. The anchoring system 1420 is joined to the absorbent core 1490. The anchoring system 1420 is configured for use in a disposable wearable absorbent article with a front and back, as described herein. The absorbent core 1490 includes a front portion 1494 disposed in the front, a crotch region 1495, and a back portion 1496 disposed in the back. The anchoring system 1420 includes a first CAM 1430 with a first end 1431 joined to the front portion 1494, a first middle 1435 disposed across the back, and a second end 1439 joined to the front portion 1494. The first end 1431 is directly connected to the front portion 1494 at a first location 1491 and the second end 1439 is directly connected to the front portion 1494 at a second location 1492 that is laterally spaced apart from the first location 1491. The anchoring system 1420 includes a third LDE 1482 with third LDE ends 1481 and 1483 and a fourth LDE with fourth LDE ends. The third LDE end 1481 of the third LDE 1482 is directly connected to the first middle 1435 and the third LDE end 1483 is directly connected to the back portion 1496 at the a third LDE location 1498. A fourth LDE end of the fourth LDE is directly connected to the first middle 1435 and a fourth LDE end of the fourth LDE is directly connected to the back portion 1496 at a fourth LDE location. In various embodiments of the anchoring system 1420, more or fewer LDEs can be used.

Figure 15A:
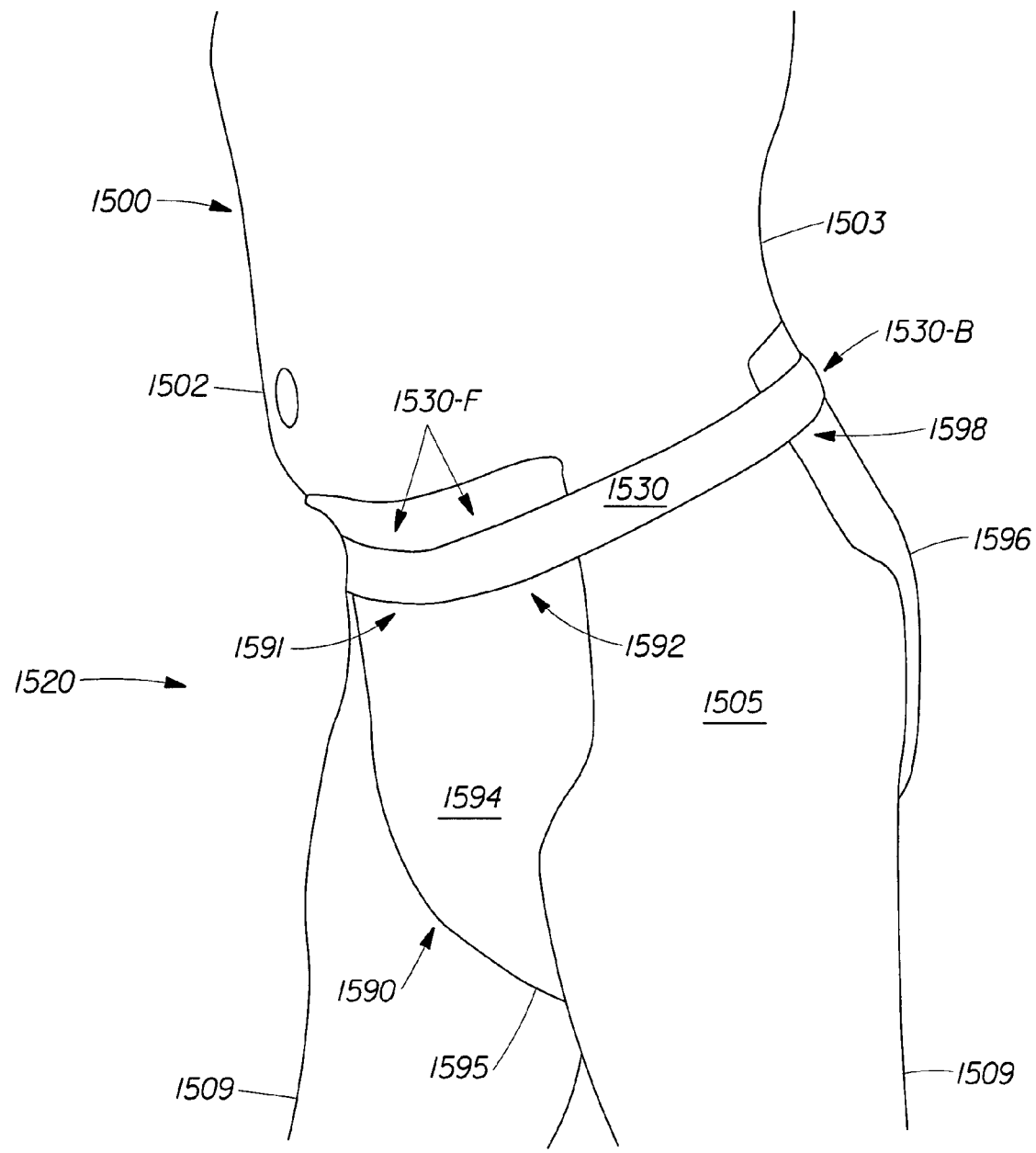
FIG. 15A illustrates a perspective view of an embodiment of an anchoring system and an absorbent core for use in a disposable wearable absorbent article, as worn on a wearer, according to the present disclosure.

FIG. 15A illustrates a perspective view of an embodiment of an anchoring system 1520 and an absorbent core 1590 for use in a disposable wearable absorbent article, as worn on a wearer 1500, according to the present disclosure. The wearer 1500 includes a belly 1502, a back 1503, a hip 1505, and upper legs 1509. The anchoring system 1520 is joined to the absorbent core 1590. The anchoring system 1520 is configured for use in a disposable wearable absorbent article with a front and back, as described herein. The absorbent core 1590 includes a front portion 1594 disposed in the front, a crotch region 1595, and a back portion 1596 disposed in the back. The anchoring system 1520 includes a continuous CAM 1530 joined to the front portion 1594 and the back portion 1596. The continuous CAM 1530 includes a front portion of the continuous CAM 1530-F disposed across the front and a back portion of the continuous CAM 1530-B disposed across the back. The front portion of the continuous CAM 1530-F is directly connected to the front portion 1594 at a first location 1591 and a second location 1592. The back portion of the continuous CAM 1530-B is directly connected to the back portion 1596 at a third location 1598 and a fourth location. The anchoring system 1520 can be included in a disposable wearable absorbent article with an outer cover configured to stretch in at least one direction, and the anchoring system 1520 can be joined to the outer cover. The front portion of the continuous CAM 1530-F is substantially parallel to a lateral centerline of a disposable wearable absorbent article in which the anchoring system 1520 can be used. The back portion of the continuous CAM 1530-B is also substantially parallel to the lateral centerline.

Figure 15B:
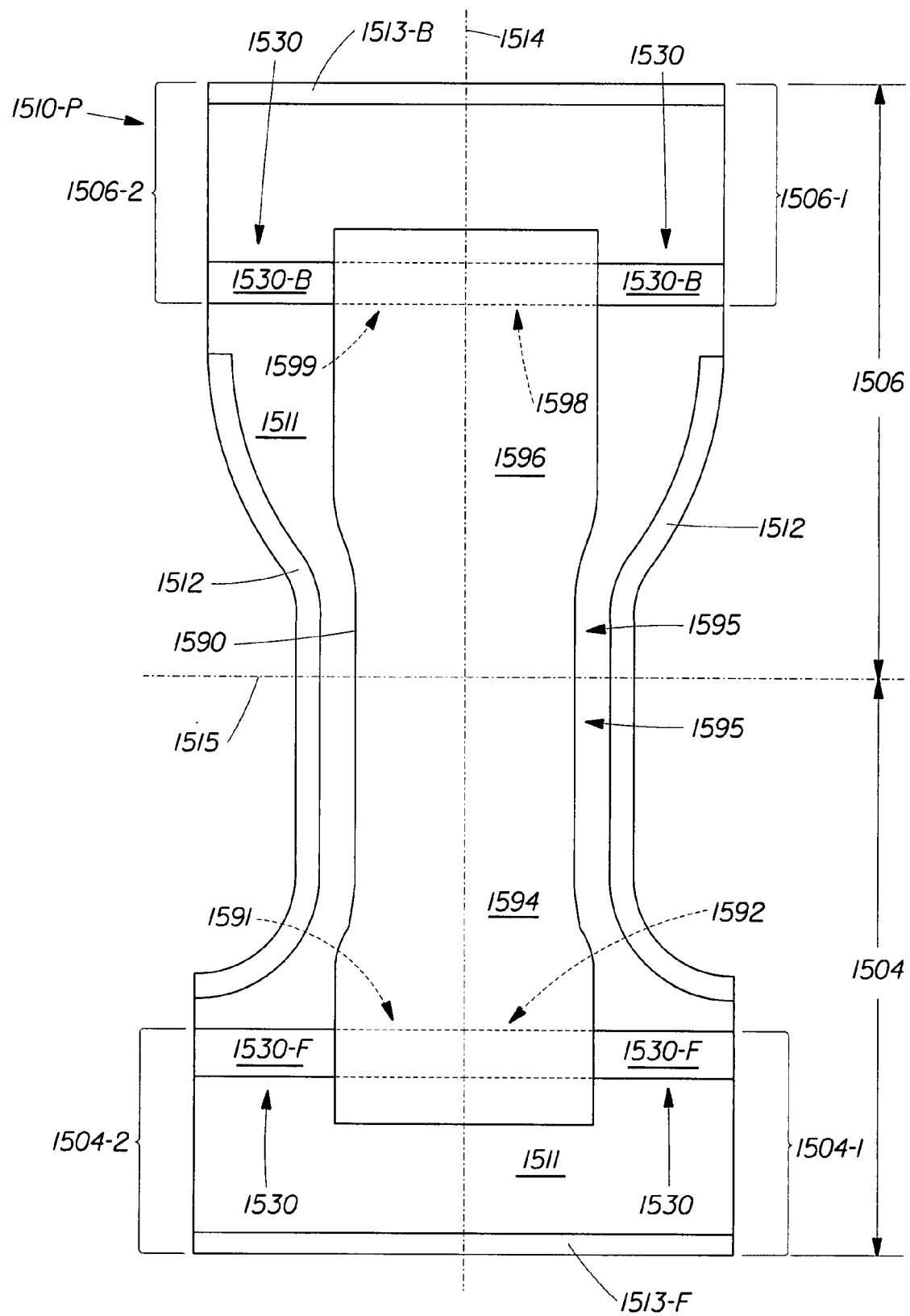
FIG. 15B illustrates a plan view of an embodiment of a pant-type disposable wearable absorbent article including the anchoring system of the embodiment of FIG. 15A, according to the present disclosure.

FIG. 15B illustrates a plan view of an embodiment of a pant-type disposable wearable absorbent article 1510-P including the anchoring system 1520 of the embodiment of FIG. 15A, according to the present disclosure. The pant-type disposable wearable absorbent article 1510-P includes a front 1504 with a first front side interface 1504-1 and a second front side interface 1504-2 and a back 1506 with a first back side interface 1506-1 and a second back side interface 1506-2. The first front side interface 1504-1 and the first back side interface 1506-1 can be joined to form a first side interface between the front 1504 and the back 1506. The second front side interface 1504-2 and the second back side interface 1506-2 can also be joined to form a second side interface between the front 1504 and the back 1506. Thus, the first and second side interfaces can each carry tension for the first CAM 1550 and/or the second CAM 1560 between the front 1504 and the back 1506.

The pant-type disposable wearable absorbent article 1510-P also includes a chassis 1511 with an outer cover configured to stretch in at least one direction, leg bands 1512, a waistband with a front portion of the waistband 1513-F and a back portion of the waistband 1513-B, a longitudinal centerline 1514, and a lateral centerline 1515. The lateral centerline 1515 forms a boundary between the front 1504 and the back 1506 in the pant-type disposable wearable absorbent article 1510-P. The pant-type disposable wearable absorbent article 1510-P includes the absorbent core 1590 with the front portion 1594 disposed in the front 1504, the crotch region 1595 disposed generally around the lateral centerline 1515, and the back portion 1596 disposed in the back 1506. The anchoring system 1520 is joined to the absorbent core 1590.

The anchoring system 1520 includes the continuous CAM 1530 joined to the front portion 1594 and the back portion 1596. The continuous CAM 1530 includes the front portion of the continuous CAM 1530-F disposed across the front 1504 and the back portion of the continuous CAM 1530-B disposed across the back 1506. The front portion of the continuous CAM 1530-F is directly connected to the front portion 1594 of the absorbent core 1590 at the first location 1591 and the second location 1592. The back portion of the continuous CAM 1530-B is joined to the back portion 1596 of the absorbent core 1590 at the third location 1598 and the fourth location 1599.

In various embodiments, the anchoring system 1520 can alternatively include a first portion of a continuous CAM configured as described in connection with a front portion of a continuous CAM 1630-F of the embodiment of FIGS. 16A and 16B or with a front portion of a continuous CAM 1730-F of the embodiment of FIG. 17, as will be understood by one of ordinary skill in the art. Also in various embodiments, the anchoring system 1520 can alternatively include a back portion of a continuous CAM configured as described in connection with a back portion of a continuous CAM 1630-B of the embodiment of FIGS. 16A and 16B or with a back portion of a continuous CAM 1730-B of the embodiment of FIG. 17, as will be understood by one of ordinary skill in the art.

Figure 16A:
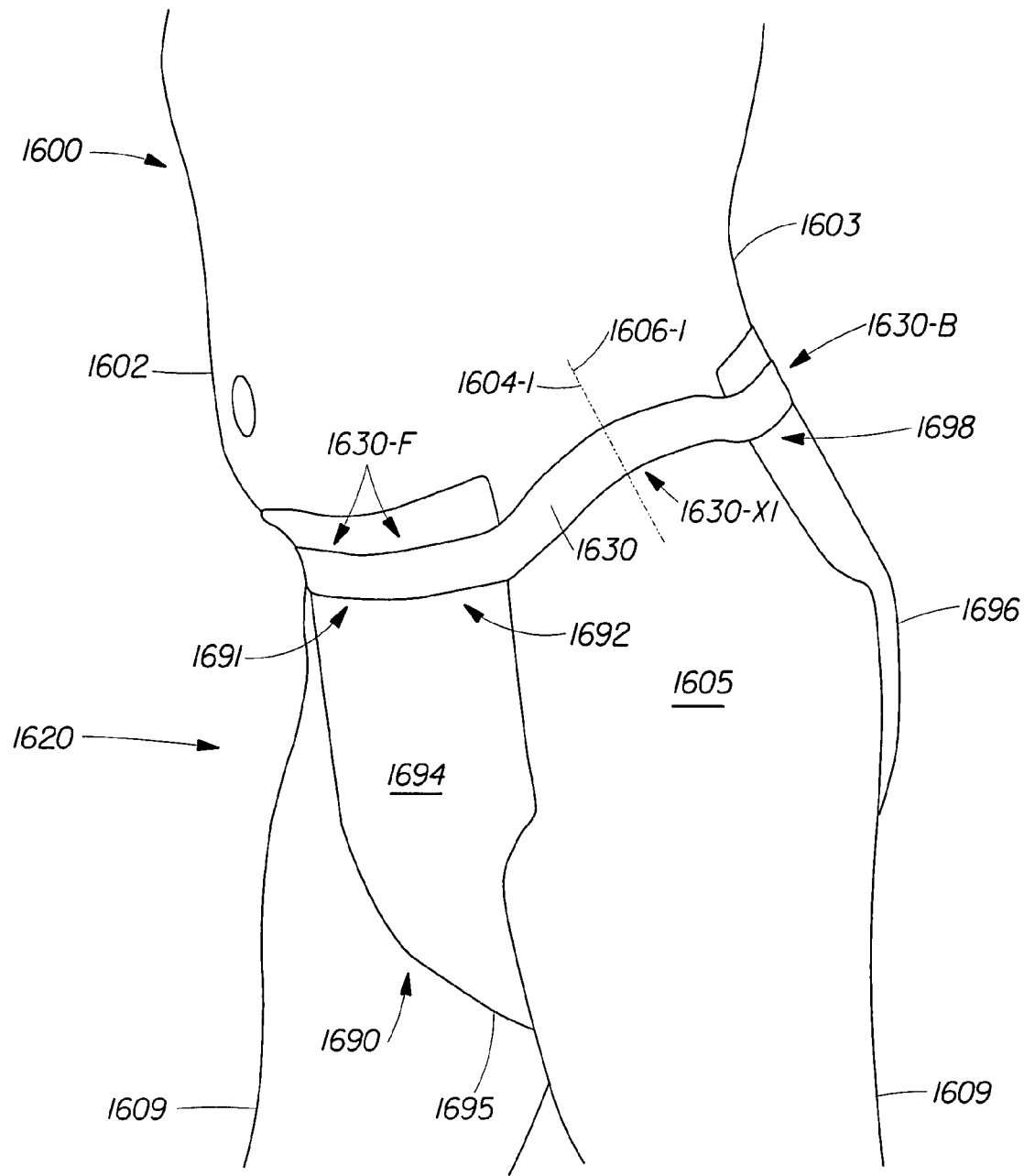
FIG. 16A illustrates a perspective view of an embodiment of an anchoring system and an absorbent core for use in a disposable wearable absorbent article, as worn on a wearer, according to the present disclosure.

FIG. 16A illustrates a perspective view of an embodiment of an anchoring system 1620 and an absorbent core 1690 for use in a disposable wearable absorbent article, as worn on a wearer 1600, according to the present disclosure. The wearer 1600 includes a belly 1602, a back 1603, a hip 1605, and upper legs 1609. The anchoring system 1620 is joined to the absorbent core 1690. The anchoring system 1620 is configured for use in a disposable wearable absorbent article with a front and back, as described herein. The absorbent core 1690 includes the front portion 1694 disposed in the front, a crotch region 1695, and the back portion 1696 disposed in the back. The anchoring system 1620 includes a continuous CAM 1630 joined to the front portion 1694 and the back portion 1696. The continuous CAM 1630 includes a front portion of the continuous CAM 1630-F disposed across the front and a back portion of the continuous CAM 1630-B disposed across the back. The anchoring CAM 1630 also includes a first front side interface 1604-1 and a first back side interface 1606-1 joined to form a first side interface between the front and the back. The continuous CAM 1630 crosses the first side interface at a first side crossing location 1630-X1. The front portion of the continuous CAM 1630-F is directly connected to the front portion 1694 at a first location 1691 and a second location 1692. The back portion of the continuous CAM 1630-B is joined to the back portion 1696 at a third location 1698 and a fourth location. The anchoring system 1620 can be included in a disposable wearable absorbent article with an outer cover configured to stretch in at least one direction, and the anchoring system 1620 can be joined to the outer cover. The continuous CAM 1630 is directly connected to the front portion 1694 at the first location 1691 and the second location 1692, each of which is longitudinally inboard to the first side crossing location 1630-X1.

Figure 16B:
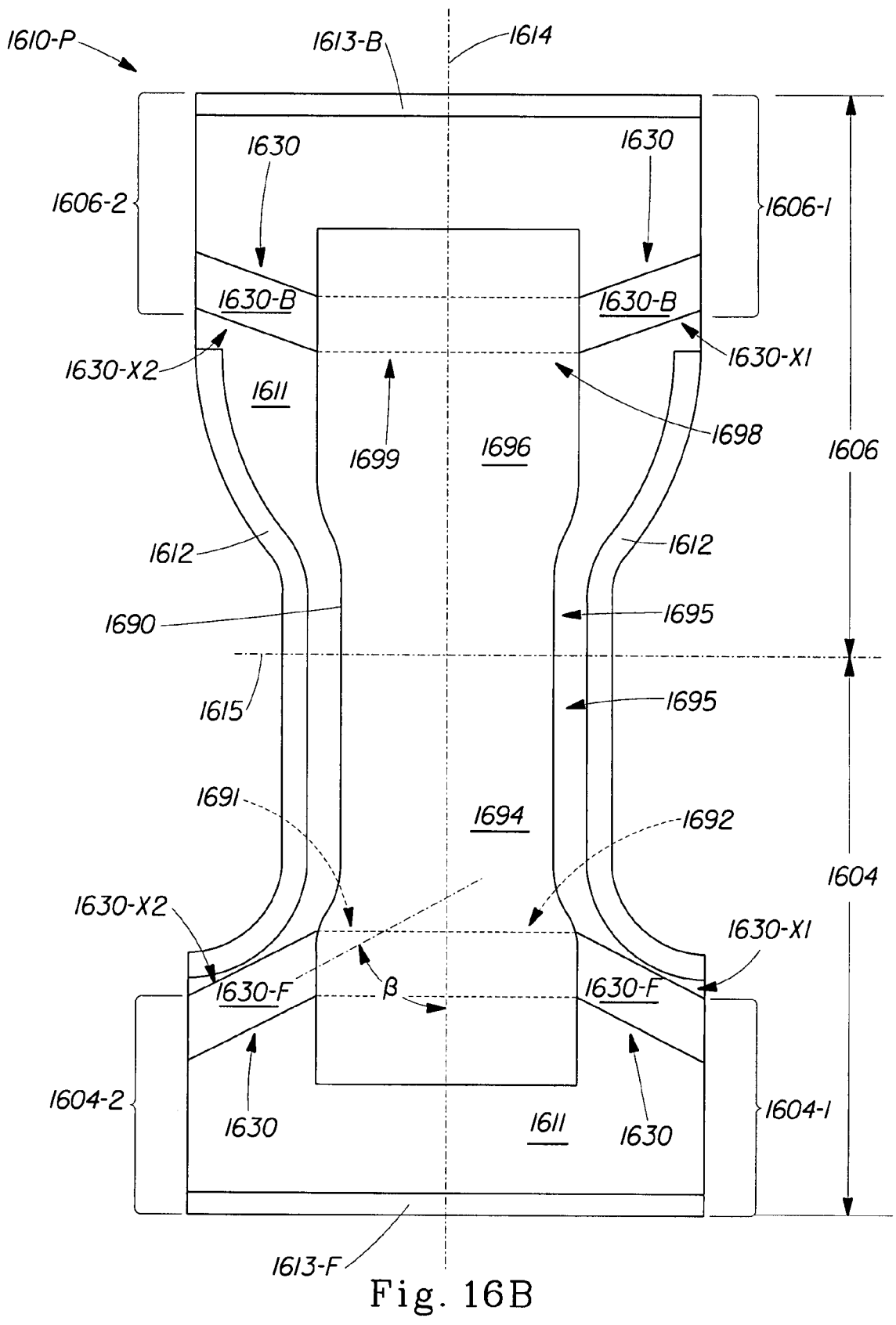
FIG. 16B illustrates a plan view of an embodiment of a pant-type disposable wearable absorbent article including the anchoring system of the embodiment of FIG. 16A, according to the present disclosure.

FIG. 16B illustrates a plan view of an embodiment of a pant-type disposable wearable absorbent article 1610-P including the anchoring system 1620 of the embodiment of FIG. 16A, according to the present disclosure. The pant-type disposable wearable absorbent article 1610-P includes a front 1604 with the first front side interface 1604-1 and a second front side interface 1604-2 and a back 1606 with the first back side interface 1606-1 and a second back side interface 1606-2. The first front side interface 1604-1 and the first back side interface 1606-1 can be joined to form a first side interface between the front 1604 and the back 1606. The second front side interface 1604-2 and the second back side interface 1606-2 can also be joined to form a second side interface between the front 1604 and the back 1606. Thus, the first and second side interfaces can each carry tension for the first CAM 1650 and/or the second CAM 1660 between the front 1604 and the back 1606.

The pant-type disposable wearable absorbent article 1610-P also includes a chassis 1611 with an outer cover configured to stretch in at least one direction, leg bands 1612, a waistband with a front portion of the waistband 1613-F and a back portion of the waistband 1613-B, a longitudinal centerline 1614, and a lateral centerline 1615. The lateral centerline 1615 forms a boundary between the front 1604 and the back 1606 in the pant-type disposable wearable absorbent article 1610-P. The pant-type disposable wearable absorbent article 1610-P includes the absorbent core 1690 with the front portion 1694 disposed in the front 1604, the crotch region 1695 disposed generally around the lateral centerline 1615, and the back portion 1696 disposed in the back 1606. The anchoring system 1620 is joined to the absorbent core 1690.

The anchoring system 1620 includes the continuous CAM 1630 joined to the front portion 1694 and the back portion 1696 of the absorbent core 1690. The continuous CAM 1630 includes the front portion of the continuous CAM 1630-F disposed across the front 1604 and the back portion of the continuous CAM 1630-B disposed across the back 1606. The front portion of the continuous CAM 1630-F is directly connected to the front portion 1694 of the absorbent core 1690 at the first location 1691 and the second location 1692. The back portion of the continuous CAM 1630-B is joined to the back portion 1696 of the absorbent core 1690 at the third location 1698 and the fourth location 1699.

The continuous CAM 1630 crosses the first side interface at a first side crossing location 1630-X1 and crosses the second side interface at a second side crossing location 1630-X2. The continuous CAM 1630 is directly connected to the front portion 1694 of the absorbent core 1690 at the first location 1691 and the second location 1692, each of which is longitudinally inboard to the side crossing locations 1630-X1 and 1630-X2. In the embodiment of FIG. 16B, a portion of the continuous CAM 1630 between the second side crossing location 1630-X2 and the first location 1691 is angled with respect to the longitudinal centerline 1614 and the lateral centerline 1615. The angular relationship between that portion of the continuous CAM 1630 and the longitudinal centerline is illustrated in FIG. 16B by the angle Beta. A portion of the continuous CAM 1630 between the first side crossing location 1630-X1 and the second location 1692 is also angled with respect to the longitudinal centerline 1614 and the lateral centerline 1615. Similar angled relationships for portions of the continuous CAM 1630 are also present in the back 1606 of the pant-type disposable wearable absorbent article 1610-P. In some embodiments, one or more portions of the continuous CAM can also be curved. In various embodiments, either the first location 1691 or the second location 1691 can be longitudinally inboard to the first side crossing location 1630-X1 or the second side crossing location 1630-X2. The continuous CAM 1630 is also directly connected to the back portion 1696 of the absorbent core 1690 at the third location 1698 and the fourth location 1699, each of which is longitudinally inboard to the side crossing locations 1630-X1 and 1630-X2. In various embodiments, the anchoring system 1620 can be configured such that either the third location 1698 or the fourth location 1699 can be longitudinally inboard to the first side crossing location 1630-X1 or the second side crossing location 1630-X2. In an alternative embodiment, the continuous CAM 1630 can be directly connected to the back portion 1696 of the absorbent core 1690 at one or more locations that are longitudinally outboard from the first side crossing locations 1630-X1 and/or the second side crossing location 1630-X2.

In various embodiments, the anchoring system 1620 can alternatively include a front portion of a continuous CAM configured as described in connection with the front portion of the continuous CAM 1530-F of the embodiment of FIGS. 15A and 15B or with the front portion of the continuous CAM 1730-F of the embodiment of FIG. 17, as will be understood by one of ordinary skill in the art. Also in various embodiments, the anchoring system 1620 can alternatively include a back portion of a continuous CAM configured as described in connection with the back portion of the continuous CAM 1530-B of the embodiment of FIGS. 15A and 15B or with the back portion of the continuous CAM 1730-B of the embodiment of FIG. 17, as will be understood by one of ordinary skill in the art.

Figure 17:
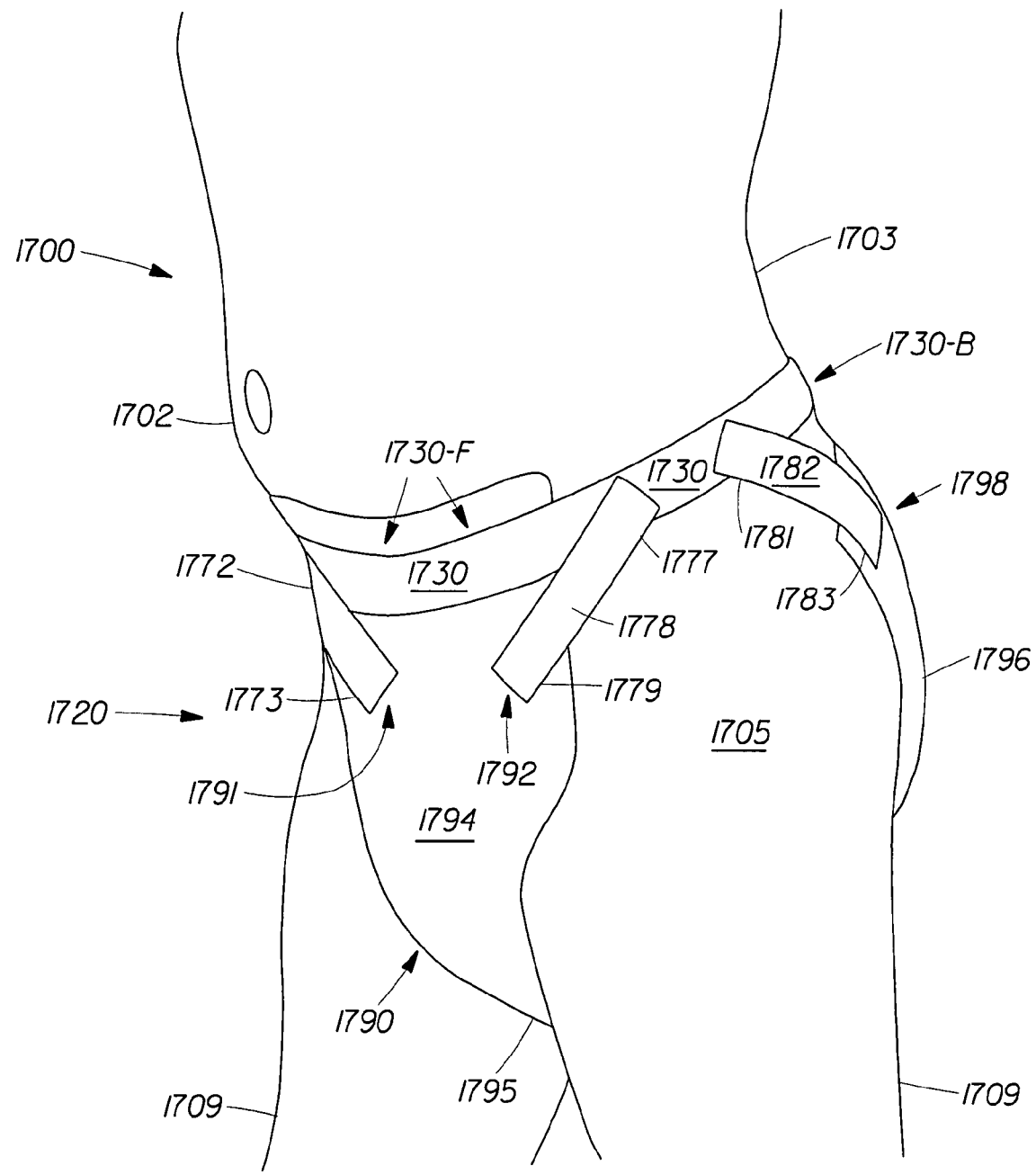
FIG. 17 illustrates a perspective view of an embodiment of an anchoring system and an absorbent core for use in a disposable wearable absorbent article, as worn on a wearer, according to the present disclosure.

FIG. 17 illustrates a perspective view of an embodiment of an anchoring system 1720 and an absorbent core 1790 for use in a disposable wearable absorbent article, as worn on a wearer 1700, according to the present disclosure. The wearer 1700 includes a belly 1702, a back 1703, a hip 1705, and upper legs 1709. The anchoring system 1720 is joined to the absorbent core 1790. The anchoring system 1720 is configured for use in a disposable wearable absorbent article with a front and back, as described herein. The absorbent core 1790 includes the front portion 1794 disposed in the front, a crotch region 1795, and the back portion 1796 disposed in the back. The anchoring system 1720 includes a continuous CAM 1730 joined to the front portion 1794 and the back portion 1796. The continuous CAM 1730 includes a front portion of the continuous CAM 1730-F disposed across the front and a back portion of the continuous CAM 1730-B disposed across the back. The anchoring system 1720 can be included in a disposable wearable absorbent article with an outer cover configured to stretch in at least one direction, and the anchoring system 1720 can be joined to the outer cover.

The anchoring system 1720 also includes a first LDE 1772 with a first LDE end 1773, a second LDE 1778 with second LDE ends 1777 and 1779, a third LDE 1782 with third LDE ends 1781 and 1783, and a fourth LDE with fourth LDE ends. The first LDE end 1773 of the first LDE 1772 is directly connected to the front portion 1794 of the absorbent core 1790 at a first location 1791 and a first LDE end of the first LDE 1772 is directly connected to the front portion of the continuous CAM 1730-F. The second LDE end 1779 of the second LDE 1778 is directly connected to the front portion 1794 of the absorbent core 1790 at a second location 1792 and the second LDE end 1777 of the second LDE 1778 is directly connected to the front portion of the continuous CAM 1730-F. The third LDE end 1783 of the third LDE 1782 is directly connected to the back portion 1796 of the absorbent core 1790 at a third location 1798 and the third LDE end 1781 of the third LDE 1782 is directly connected to the back portion of the continuous CAM 1730-B. A fourth end of the fourth LDE is directly connected to the back portion 1796 of the absorbent core 1790 and a fourth end of the fourth LDE is directly connected to the back portion of the continuous CAM 1730-B. In various embodiments of the anchoring system 1720, more or fewer LDEs can be used.

In various embodiments, the anchoring system 1720 can alternatively include a front portion of a continuous CAM configured as described in connection with the front portion of the continuous CAM 1530-F of the embodiment of FIGS. 15A and 15B or with the front portion of the continuous CAM 1630-F of the embodiment of FIGS. 16A and 16B, as will be understood by one of ordinary skill in the art. Also in various embodiments, the anchoring system 1620 can alternatively include a back portion of a continuous CAM configured as described in connection with the back portion of the continuous CAM 1530-B of the embodiment of FIGS. 15A and 15B or with the back portion of the continuous CAM 1630-B of the embodiment of FIGS. 16A and 16B, as will be understood by one of ordinary skill in the art.

Embodiments of the present disclosure include disposable wearable absorbent articles with anchoring systems that fit wearers well. In some embodiments, these articles can include stretchable outer covers. The designs of these disposable wearable absorbent articles allow the articles to have an underwear-like appearance that conforms to a wearer's body as the wearer moves. The designs of these articles also help prevent the articles from sagging or slipping down on a wearer. As a result, the disposable wearable absorbent articles of the present disclosure can feel comfortable, look attractive, and perform well as the articles tend to fit snugly, stay in place, and not leak.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and the scope of the invention. It is therefore intended to cover in the appended claims all such changes and modifications that are within the scope of this invention.

What is claimed is:

1. A disposable wearable absorbent article comprising:
    a chassis;
    a front;
    a back; and
    an anchoring system;
    wherein the chassis includes a topsheet, an outer cover, and an absorbent core disposed between the topsheet and the outer cover;
    wherein the chassis defines a waist opening and a pair of leg openings;
    wherein the absorbent core includes a front portion disposed in the front and a back portion disposed in the back;
    wherein the anchoring system includes:
        a first circumferential anchoring member with:
            a first end overlapping the front portion and joined to the front portion at a first location,
            a first middle disposed at least in part across the back, and
            a second end overlapping the front portion and joined to the front portion at a second location; and
        a second circumferential anchoring member with:
            a third end overlapping the back portion and joined to the back portion at a third location,
            a second middle disposed at least in part across the front, and
            a fourth end overlapping the back portion and joined to the back portion at a fourth location.

2. The disposable wearable absorbent article of claim 1, wherein:
    the first end is directly connected to the front portion; and
    the second end is directly connected to the front portion.

3. The disposable wearable absorbent article of claim 1, including:
    a first side disposed between the front and the back;
    a second side disposed between the front and the back; and
    wherein the first middle is joined to the second middle on the first side and on the second side.

4. The disposable wearable absorbent article of claim 1, wherein:
    the third end is directly connected to the back portion; and
    the fourth end is directly connected to the back portion.

5. The disposable wearable absorbent article of claim 1, wherein the first location at least partially overlaps the second location.

6. The disposable wearable absorbent article of claim 1, wherein the third location at least partially overlaps the fourth location.

7. A disposable wearable absorbent article comprising:
a chassis;
a front;
a back;
a first side disposed between the front and the back;
a second side disposed between the front and the back; and
an anchoring system;
wherein the chassis includes a topsheet, an outer cover, and an absorbent core disposed between the topsheet and the outer cover;
wherein the chassis defines a waist opening and a pair of leg openings;
wherein the absorbent core includes a front portion disposed in the front and a back portion disposed in the back;
wherein the anchoring system includes:
a first circumferential anchoring member with a first end joined to the front portion at a first location, a first middle disposed at least in part across the first side, and a fourth end joined to the back portion at a fourth location;
a second circumferential anchoring member with a second end joined to the front portion at a second location, a second middle disposed at least in part across the second side, and a third end joined to the back portion at a third location; and
a stabilizing band, directly connected to the first circumferential anchoring member and directly connected to the second circumferential anchoring member.

8. The disposable wearable absorbent article of claim 7, wherein the stabilizing band is a continuous stabilizing band disposed continuously across the front and the back.

9. The disposable wearable absorbent article of claim 7, wherein the stabilizing band is a front stabilizing band disposed at least in part in the front.

10. The disposable wearable absorbent article of claim 7, wherein:
the first end is directly connected to the front portion; and
the second end is directly connected to the front portion.

11. The disposable wearable absorbent article of claim 7, wherein:
the third end is directly connected to the back portion; and
the fourth end is directly connected to the back portion.

12. The disposable wearable absorbent article of claim 7, wherein the stabilizing band is a back stabilizing band disposed at least in part in the back.

13. The disposable wearable absorbent article of claim 7, wherein the first location at least partially overlaps the second location.

14. The disposable wearable absorbent article of claim 7, wherein the third location at least partially overlaps the fourth location.

* * * * *